United States Patent
Zhou et al.

(10) Patent No.: US 9,159,936 B2
(45) Date of Patent: Oct. 13, 2015

(54) ORGANIC ELECTROLUMINESCENT MATERIAL CONTAINING IRIDIUM, PREPARATION METHOD THEREOF AND ORGANIC ELECTROLUMINESCENT ELEMENT

(75) Inventors: Mingjie Zhou, Guangdong (CN); Ping Wang, Guangdong (CN); Juanjuan Zhang, Guangdong (CN); Lusheng Liang, Guangdong (CN)

(73) Assignee: Ocean's King Lighting Science & Technology Co., Ltd., Guangdong (CN)

( * ) Notice: Subject to any disclaimer, the term of this patent is extended or adjusted under 35 U.S.C. 154(b) by 325 days.

(21) Appl. No.: 13/885,313

(22) PCT Filed: Nov. 25, 2010

(86) PCT No.: PCT/CN2010/079147
§ 371 (c)(1),
(2), (4) Date: May 14, 2013

(87) PCT Pub. No.: WO2012/068736
PCT Pub. Date: May 31, 2012

(65) Prior Publication Data
US 2013/0231487 A1    Sep. 5, 2013

(51) Int. Cl.
C07F 15/00   (2006.01)
H01L 51/00   (2006.01)
C09K 11/06   (2006.01)
H05B 33/10   (2006.01)

(52) U.S. Cl.
CPC ........ *H01L 51/0085* (2013.01); *C07F 15/0033* (2013.01); *C09K 11/06* (2013.01); *H05B 33/10* (2013.01); *C09K 2211/1007* (2013.01); *C09K 2211/1011* (2013.01); *C09K 2211/1044* (2013.01); *C09K 2211/185* (2013.01)

(58) Field of Classification Search
CPC .................................................. C07F 15/0033
See application file for complete search history.

(56) References Cited

U.S. PATENT DOCUMENTS 7,154,114 B2 * 12/2006 Brooks et al. ................... 257/40
2005/0258742 A1  11/2005 Tsai et al.
2005/0260447 A1  11/2005 Brooks et al.

FOREIGN PATENT DOCUMENTS

WO    2005/113704 A2    12/2005

OTHER PUBLICATIONS

Communication From the Japanese Patent Office Regarding a Counterpart Foreign Application Dated (Emperor Year—Heisei 26) Jun. 10, 2014.
"Higher education planning materials Pharmaceutical Engineering Pharmaceutical: drug reaction"; by Zhao Gui Sen Li Jing Fen; ISBN 978-7-308-07866-5.
Patent Communication From the Chinese Patent Office Regarding a Counterpart Foreign Application Dated Jan. 30, 2014.

* cited by examiner

*Primary Examiner* — Joseph Kosack
(74) *Attorney, Agent, or Firm* — Rosenberg, Klein & Lee

(57) ABSTRACT

Organic electroluminescent material containing iridium of the following general formula, in which R is $C_1$-$C_8$ alkyl, is provided. The preparation method of the above organic electroluminescent material containing iridium and the organic electroluminescent element using the above organic electroluminescent material containing iridium are also provided.

8 Claims, 2 Drawing Sheets

ORGANIC ELECTROLUMINESCENT MATERIAL CONTAINING IRIDIUM, PREPARATION METHOD THEREOF AND ORGANIC ELECTROLUMINESCENT ELEMENT

FIELD OF THE INVENTION

The present disclosure relates to organic electroluminescent technical fields, and more particularly relates to an iridium containing organic electroluminescent material, preparation method thereof and an organic electroluminescent element containing the iridium containing organic electroluminescent material.

BACKGROUND OF THE INVENTION

The organic electroluminescent (EL) is a luminous phenomenon in which the organic materials convert the electrical energy directly into light energy under an electric field. In early stage, due to such reasons as high voltage of the driver system, low luminous efficiency of the device, the research on organic electroluminescent was stagnated. In 1987, Tan et al (Kodak Corporation) invented 8-hydroxyquinoline aluminum ($Alq_3$) as light-emitting materials, which can be made into a uniform, dense, high-quality thin film with aromatic diamine, such that the organic electroluminescent device was prepared with significantly increasing brightness and luminescent efficiency under low working voltage, and a research on new prologue electroluminescent materials was opened. However, due to the restriction of the spin statistics theory, the internal quantum efficiency of the fluorescent material was merely 25% in theory, thus it became a hot research directions in the field thereafter that how to make full use of the remaining 75% of the phosphorescence to achieve higher luminous efficiency. In 1997, Forrest et al discovered phosphorus electroluminescent phenomenon, and the internal quantum efficiency of the subsequently obtained organic electroluminescent material broke through the 25% limit, thus leading the research of the organic electroluminescent material into another new period.

In nowadays study of organic electroluminescent material, complexes of transition metal, such as complexes of iridium, ruthenium, platinum, etc., doped with small molecule have become a research focus. The advantages of the complexes are that they can obtain a high energy emitted from the triplet of their own, and the metal iridium (III) compounds, because of the good stability, mild reaction conditions in the synthesis process, and the high electroluminescent properties, have occupied the dominant position in the subsequent study. Nevertheless, conventional iridium containing organic electroluminescent material, such as bis[2-(2,4-difluorophenyl-yl)pyridine-N, $C^2$](pyridine-formic acid) combined iridium (FIrpic), bis[2-(2,4-difluoro-3-cyanophenyl)pyridine-N, $C^2$](four pyrazole boron) iridium (Fir6) and the like, have a poor internal quantum efficiency and electroluminescent efficiency, thus limiting the development of the research on organic electroluminescent technology.

SUMMARY OF THE INVENTION

In view of this, it is necessary to provide an iridium containing organic electroluminescent material having higher internal quantum efficiency and electroluminescence efficiency and a preparation method thereof.

An iridium containing organic electroluminescent material is represented by the following formula I:

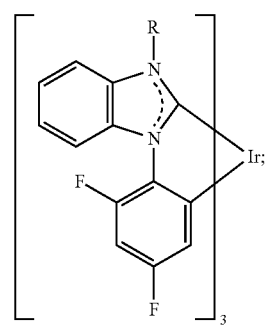

wherein R is $C_1$-$C_8$ alkyl.

The iridium containing organic electroluminescent material molecule contains benzimidazolyl with electron-transporting function, and the benzimidazolyl is also carried with alkyl group, fluorophenyl, such that it can significantly improve the electron injection and transport capacity, and has high internal quantum efficiency and electroluminescent efficiency. In addition, the molecule further contains 1-(2,4-difluorophenyl)-3-substituted benzimidazole ligand, therefore the solubility of the compounds can be regulated by changing the length of 3-position of alkyl chain, thus the applicability is enhanced.

A preparation method of an iridium containing organic electroluminescent material comprises the following steps:

step one: preparing a compound A represented by the following formula:

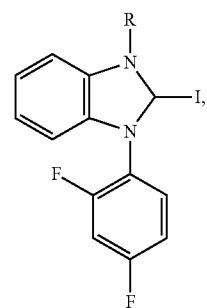

wherein R is $C_1$-$C_8$ alkyl;

step two: performing reaction between compound A and Iridium trichloride trihydrate in a solvent under anaerobic condition in presence of $Ag_2O$ catalyst to obtain a bridge compound B; the reaction equation being:

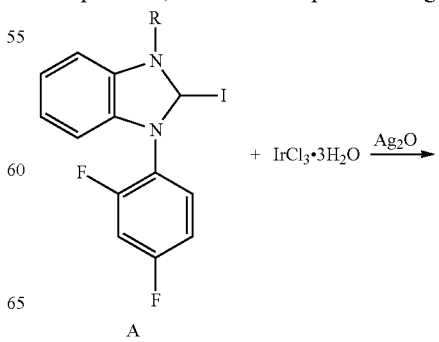

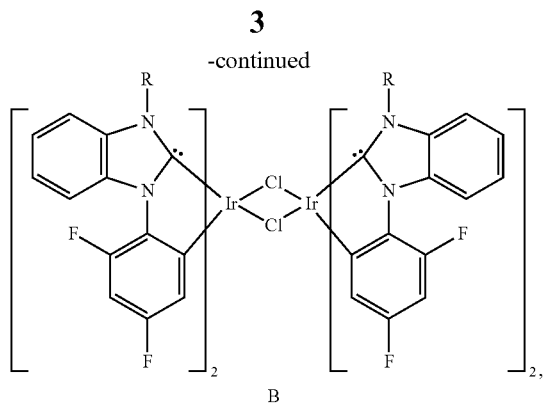

and step three: performing ligands interchange reaction between bridge compound B and compound A in a solvent under anaerobic condition in presence of Ag₂O catalyst to obtain the compound I; the reaction equation being:

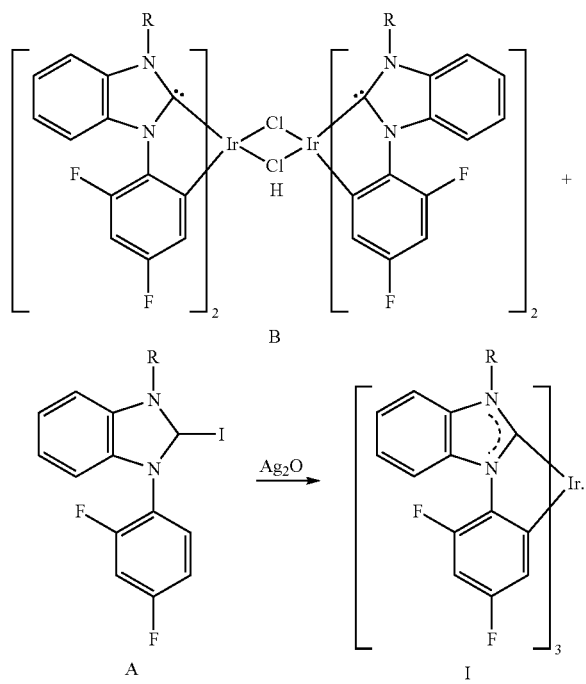

Preferably, the solvent in step two is 2-ethoxyethanol, and the reaction temperature is from 100° C. to 150° C.; the solvent in step three is 1,2-dichloroethane, and the reaction temperature is from 90° C. to 150° C.

Preferably, the step two further comprises separation and purification steps: an obtained mixture after the reaction between compound A and iridium trichloride trihydrate is firstly concentrated under reduced pressure; the concentrate is then applied to silica gel column chromatography for 2 to 3 times using dichloromethane as eluent, and the purified compound B is obtained.

Preferably, the step three further comprises separation and purification steps:

firstly, the reaction product containing the compound I is concentrated under reduced pressure to obtain a concentrated product containing Compound I;

then, the concentrated product is applied to silica gel column chromatography using dichloromethane as eluent to obtain a solid mixture containing isomer II and isomer III;

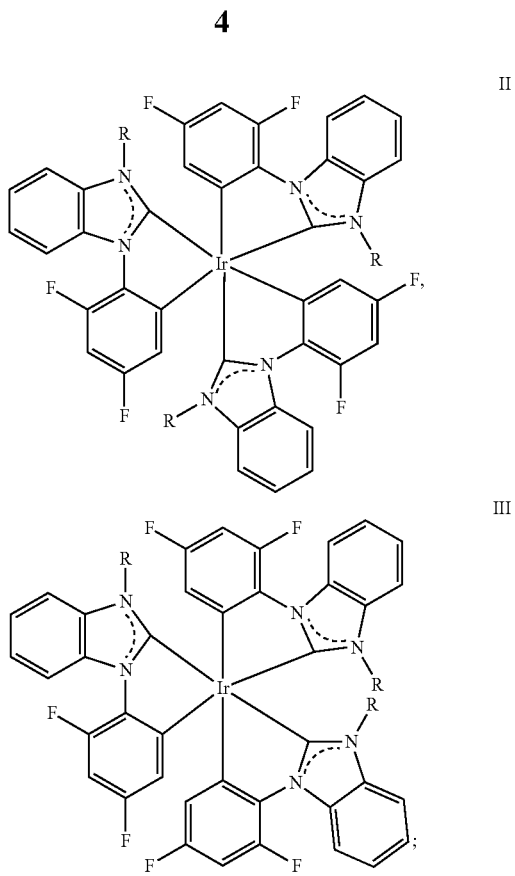

the solid mixture is applied to silica gel column chromatography using a mixture solution containing ethyl acetate and n-hexane in a volume ratio of 1:4 as eluant to obtain a purified compound III and separation residual liquid;

finally, the separation residual liquid is applied to silica gel column chromatography using a mixture solution containing ethyl acetate and n-hexane in a volume ratio of 2:3 as eluant to obtain purified compound II.

Preferably, a preparation method of the compound A comprises the following steps:

step one, providing compound C and D represented by the following formulas,

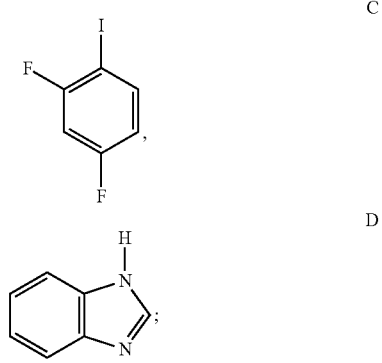

step two, performing Ullmann coupling reaction between the compound C and the compound D under anaerobic condition in presence of catalyst to obtain compound E, the reaction equation being:

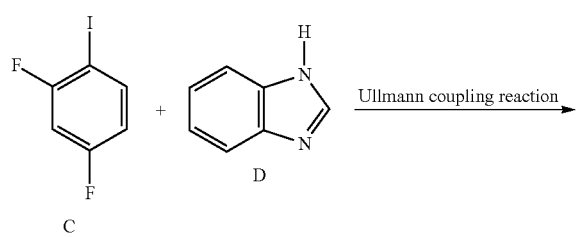

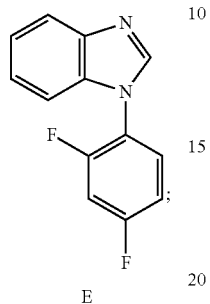

step three, reacting the compound E with an alkyl iodide in a solvent to obtain the compound A, the reaction equation being:

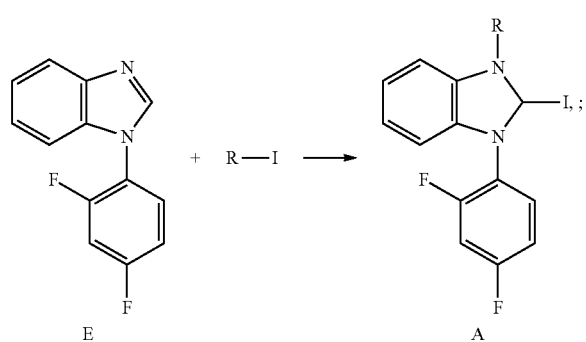

Wherein R—I is alkyl iodide, R is $C_1$-$C_8$ alkyl.

Preferably, in step two the reaction temperature of the Ullmann coupling reaction is from 100° C. to 180° C., the catalyst is a mixed catalyst composed of copper iodide, 1,10-phenanthroline and cesium carbonate, the solvent is N,N-dimethylformamide; the solvent in step three is toluene, the reaction temperature is from 25° C. to 45° C.

Preferably, the step two further comprises steps of separation and purification of compound E: an obtained mixture of the Ullmann coupling reaction is vacuum concentrated; ethyl acetate solution was added to the concentrate to produce a precipitate; the precipitate is separated by filtration and is washed with ethyl acetate, and the filtrate was collected; the filtrate is finally concentrated and is applied to silica gel column chromatography using a mixture solution containing ethyl acetate and n-hexane in a volume ratio of 2:3 as eluant, and the purified compound E is obtained.

Preferably, the step three further comprises steps of separation and purification of compound A: the crude reaction product of step three is filtrated, the filtrated precipitate is washed with toluene and dried to obtain the purified compound A.

The preparation method described above is simple, easy to operate, low equipment requirements, and can be widely used.

Furthermore, it is necessary to provide an organic electroluminescent element having higher internal quantum efficiency and electroluminescence efficiency.

An organic electroluminescent element comprises a light emitting layer, wherein the light emitting layer contains the compound I represented by the following formula I:

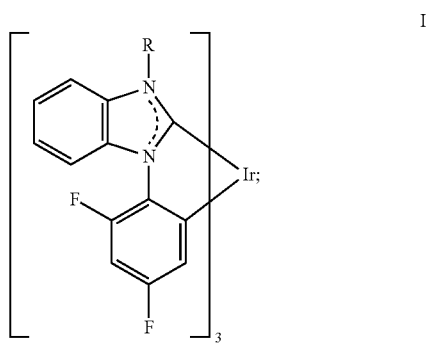

wherein R is $C_1$-$C_8$ alkyl.

The compound I has an improving compatibility with a host material in the light emitting layer of the organic electroluminescence element, thus it can be widely used as a doped object in light emitting layer to prepare a blue or white phosphorus electroluminescent element. Since the light-emitting layer containing the iridium containing organic electroluminescent material has high internal quantum efficiency and the electroluminescent efficiency, the electroluminescent element has a high energy conversion efficiency and luminous efficiency.

DETAILED DESCRIPTION

The iridium-containing organic electroluminescent material and its preparation method and application will be further described in connection with the accompanying with drawings and specific embodiments.

Metal organic complexes of iridium (Ir) is a phosphorescent light emitting material having a short phosphorescence lifetime (1-14 μs). An embodiment of an iridium containing organic electroluminescent material is represented by formula $Fir(pmb)_3$, which includes two isomers, i.e. fac-FIr$(pmb)_3$ and mer-FIr$(pmb)_3$, wherein F represents two fluorine atoms carried by specific functional groups, pmb represents 1-(2,4-difluorophenyl)-3-alkyl imidazolyl, 3-position substituent is an alkyl group of $C_1$-$C_8$. The specific structural formulas are shown as follows:

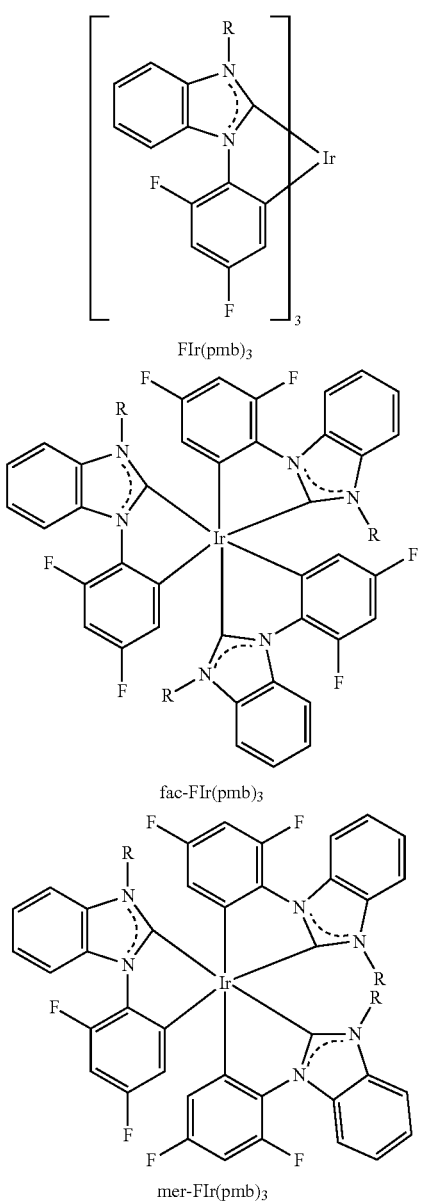

FIr(pmb)₃ fac-FIr(pmb)₃ mer-FIr(pmb)₃

Wherein R is $C_1$-$C_8$ alkyl.

The embodiment of the iridium containing organic electroluminescent material molecule contains benzimidazolyl with electron-transporting function, and the benzimidazolyl is also carried with alkyl group, fluorophenyl, such that it can significantly improve the electron injection and transport capacity, and has high internal quantum efficiency and electroluminescent efficiency. In addition, the molecule further contains 1-(2,4-difluorophenyl)-3-substituted benzimidazole ligand, therefore the solubility of the compounds can be regulated by changing the length of 3-position of alkyl chain, thus the applicability is enhanced. The iridium containing organic electroluminescent material has an improving compatibility with a host material in the light emitting layer of the organic electroluminescence element, thus it can be widely used as a doped object in light emitting layer to prepare a blue or white phosphorus electroluminescent element.

Figure 1:
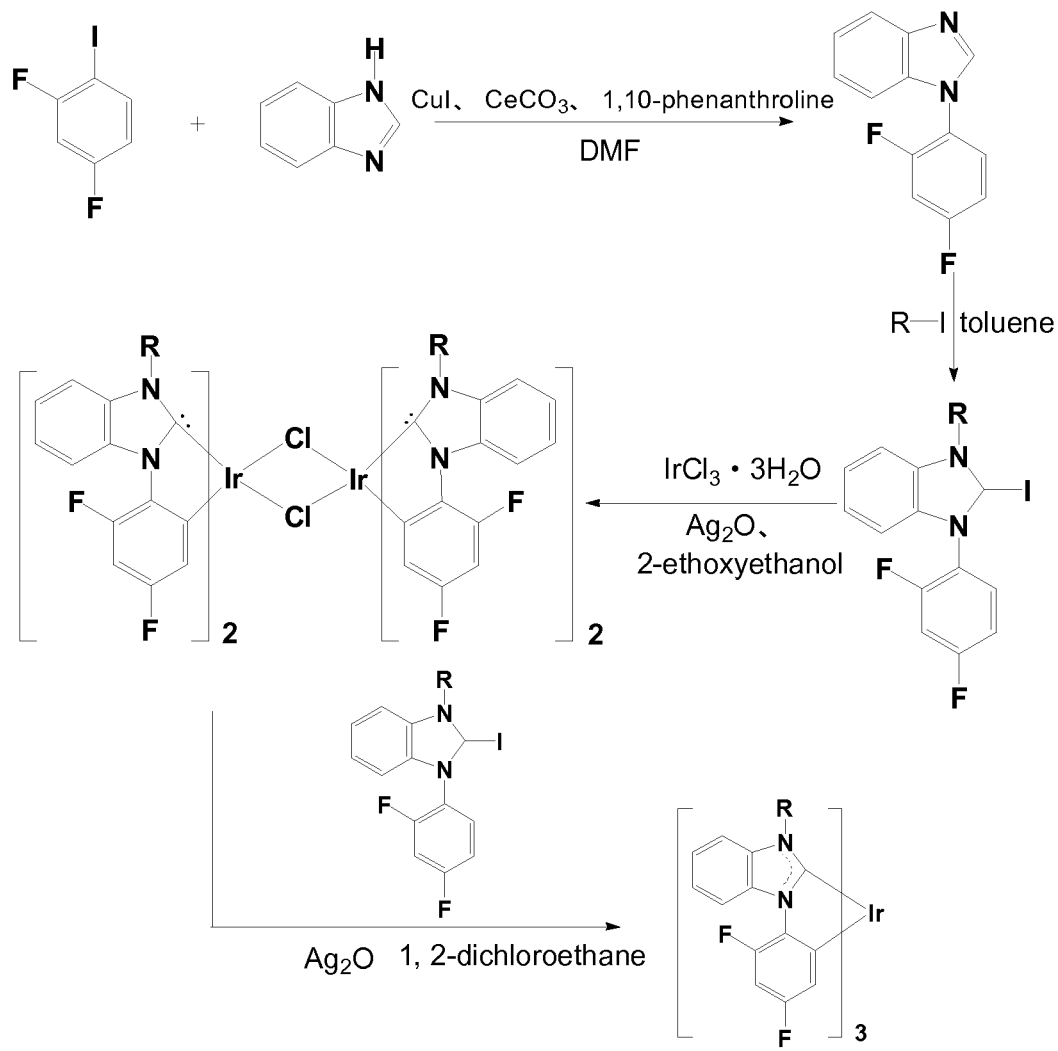
FIG. 1 is a flowchart of a preparation method of an embodiment of an organic electroluminescent material.
Figure 2:
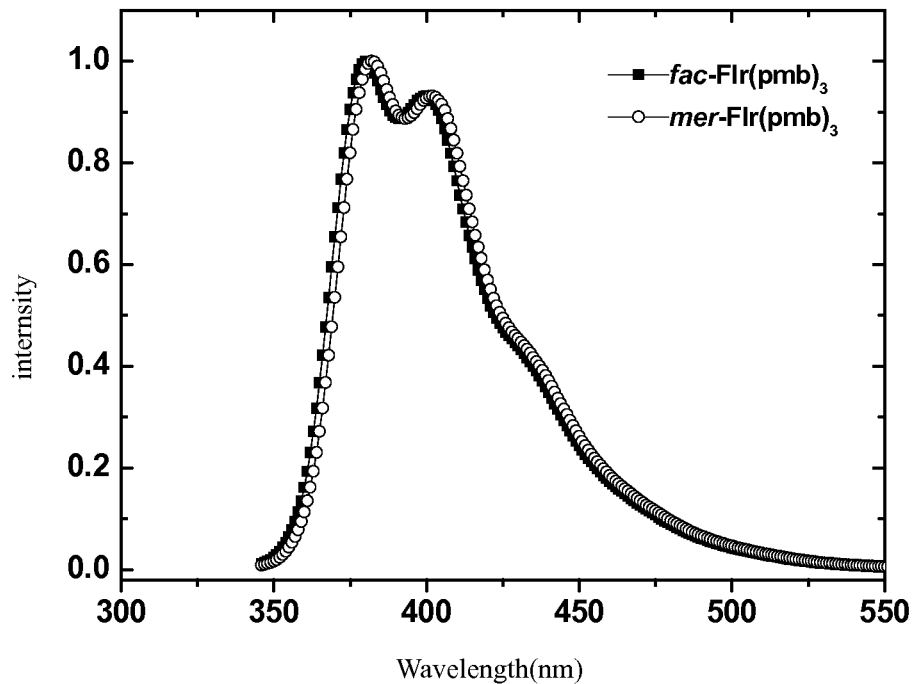
FIG. 2 is an emission spectra of the luminescent material in Example 8.

Referring to FIG. 1, a first embodiment of a preparation method of the iridium containing organic electroluminescent material specifically includes the following steps:

The following steps are carried out under anaerobic conditions (e.g. $N_2$ or inert gas atmosphere, etc.).

Step S1: In a solvent of N,N-dimethyl formamide (DMF), benzimidazole, and 2,4-difluoro-iodobenzene are subjected to a Ullmann coupling reaction in presence of a mixed catalyst containing copper iodide (CuI), 1,10-phenanthroline, and cesium carbonate ($CeCO_3$) at a temperature from 100° C. to 180° C. for the, to obtain 1-(2,4-difluorophenyl yl)benzimidazole. The reaction equation is shown as follows:

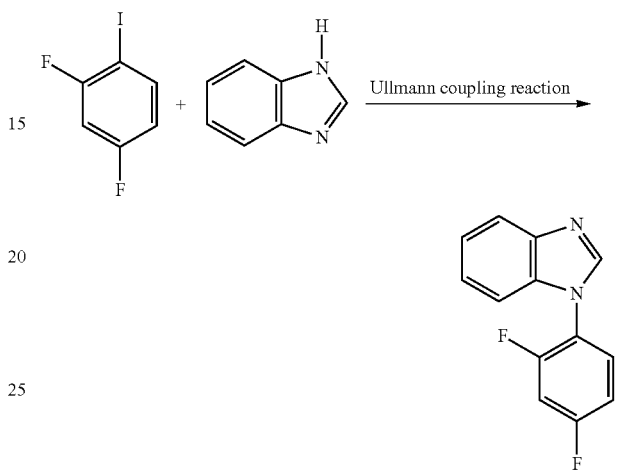

Step S2: the 1-(2,4-difluorophenyl)benzimidazole is reacted with alkyl iodide in a solvent of toluene at a temperature from 100° C. to 150° C. to obtain 1-(2,4-difluorophenyl)-3-alkyl iodide, the reaction equation is shown as follows:

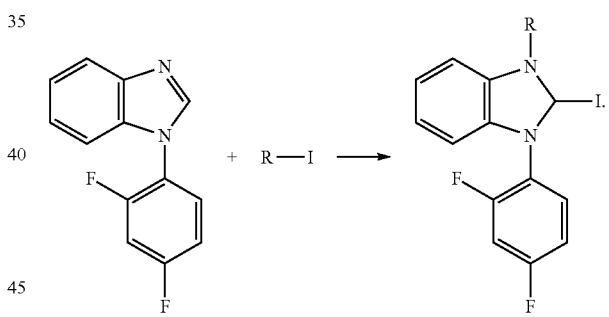

Step S3: In a reaction system using 2-ethoxyethanol as the solvent, the obtained 1-(2,4-difluorophenyl)-3-alkyl iodide is reacted with iridium trichloride trihydrate in presence of silver oxide at a temperature from 100° C. to 150° C. to obtain a bridge compound $(Fpmb)_2Ir(\mu-Cl)_2Ir(Fpmb)_2$, the reaction equation is shown as follows:

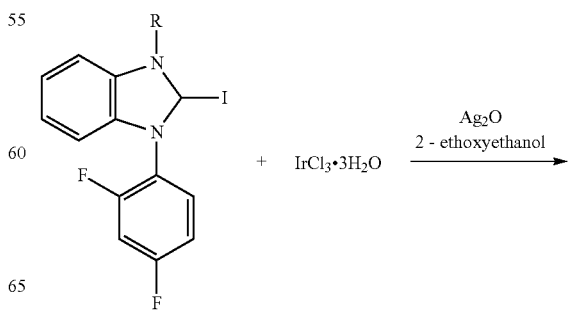

-continued

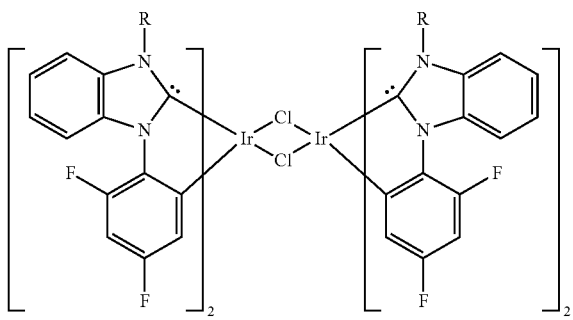

Step S4: In a reaction system using 1,2-dichloroethane as the solvent, a ligands interchange reaction is performed between compound 1-(2,4-difluorophenyl)-3-alkyl iodide and the bridge compound (Fpmb)₂Ir(μ-Cl)₂Ir(Fpmb)₂, in presence of silver oxide at a temperature from 90° C. to 150° C. to obtain the object product FIr(pmb)₃, the reaction equation is shown as follows:

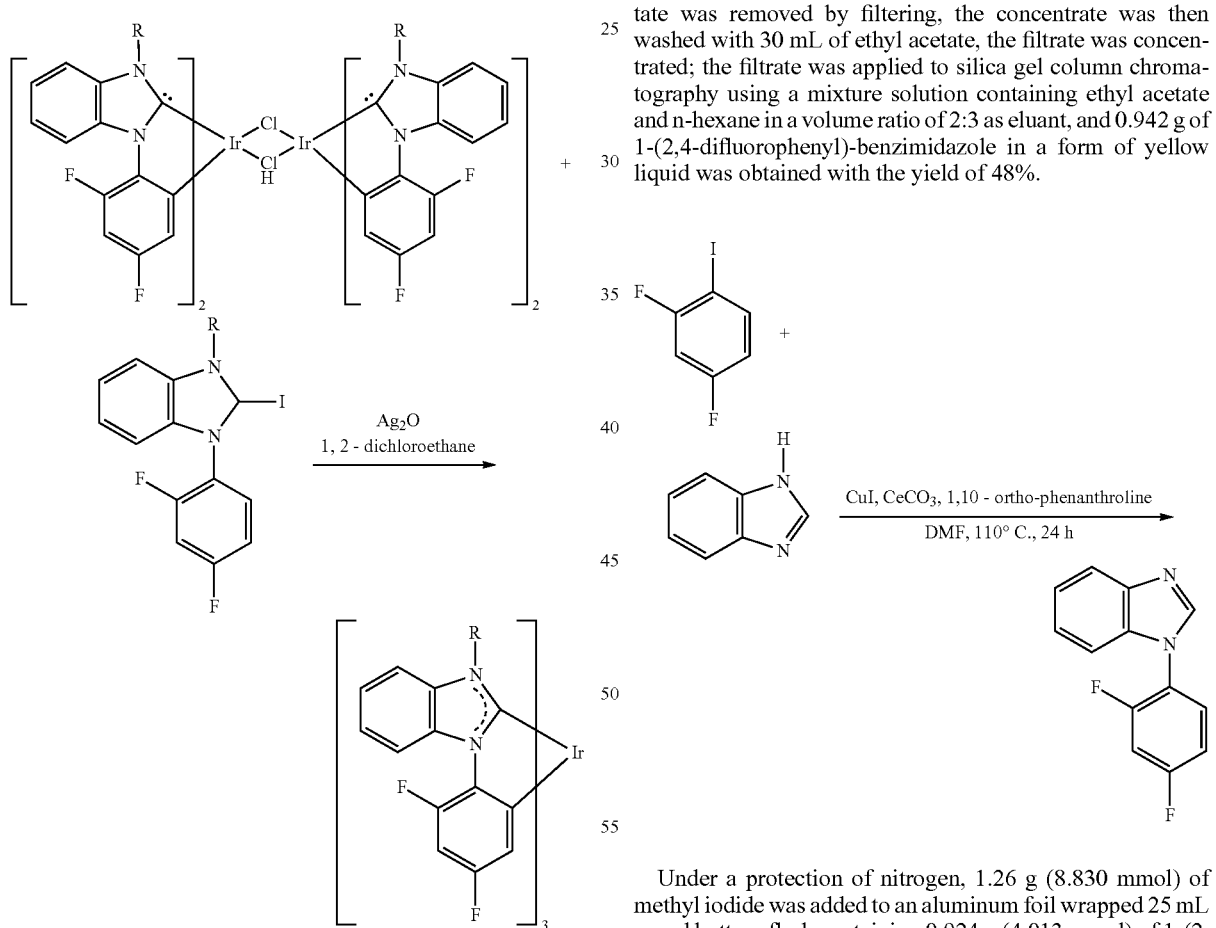

Step S5: highly purified mer-FIr(pmb)₃ and the fac-FIr (pmb)₃ can be obtained after subsequent separation and purification operations.

The preparation method described above is simple, easy to operate, low equipment requirements, and can be widely used.

Specific Examples are described as follows:

EXAMPLE 1

The synthesis of iridium(III) tris (1-(4',6'-difluorophenyl)-3-methylbenzimidazolin-2-ylidene-C,C²')

(1) The Synthesis of 1-(2,4-difluorophenyl)-3-methylbenzimidazole iodide 0.16 g (0.836 mmol) of CuI, 1.20 g (10.15 mmol) of benzimidazole and 5.70 g (17.50 mmol) of cesium carbonate ($CeCO_3$) were successively added into a 50 ml round bottom flask wrapped by aluminum foil, after introducing nitrogen for 15 minutes, 1 mL (8.36 mmol) of 2,4-difluoro-iodobenzene, 0.30 g (1.67 mmol) of 1,10-ortho-phenanthroline and 25 mL of anhydrous N,N-dimethylformamide (DMF) were successively added to the nitrogen stream to form a reaction mixture; after 30 minutes of continually introducing nitrogen to the reaction mixture, the system was heated in oil bath to 110° C. and stirred for 24 hours; after the reaction was cooled to room temperature, it was concentrated in vacuum, and 10 mL of ethyl acetate was added to the concentrate, the precipitate was removed by filtering, the concentrate was then washed with 30 mL of ethyl acetate, the filtrate was concentrated; the filtrate was applied to silica gel column chromatography using a mixture solution containing ethyl acetate and n-hexane in a volume ratio of 2:3 as eluant, and 0.942 g of 1-(2,4-difluorophenyl)-benzimidazole in a form of yellow liquid was obtained with the yield of 48%.

Under a protection of nitrogen, 1.26 g (8.830 mmol) of methyl iodide was added to an aluminum foil wrapped 25 mL round bottom flask containing 0.924 g (4.013 mmol) of 1-(2, 4-difluorophenyl)-benzimidazole, and 15 mL of toluene, the system was stirred at 30° C. for 24 hours and white precipitate was generated; the precipitate was washed with 20 mL of toluene and dried to obtain 0.882 g of 1-(2,4-difluorophenyl)-3-methyl iodide in a form of white solid with yield of 59%. The detection data of the product is as follows: ¹H NMR (400 MHz, $CDCl_3$, ppm): 9.32 (s, 1H), 8.31-8.13 (m, 3H), 7.78-7.66 (m, 4H), 4.52 (s, 3H).

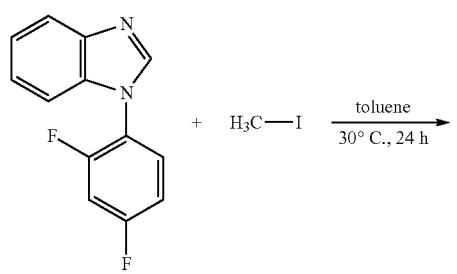

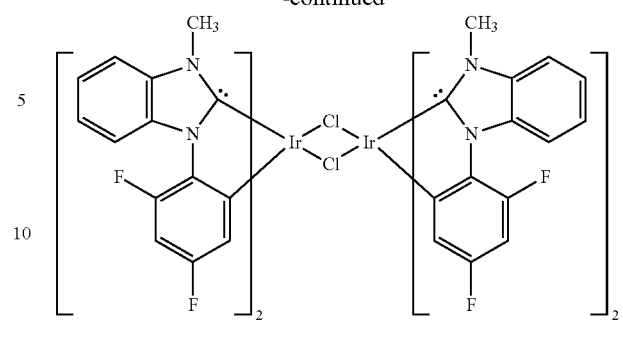

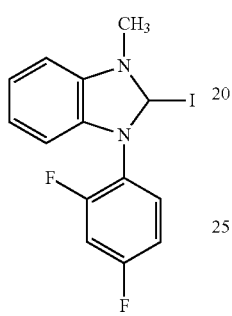

(2) The Synthesis of Bridge Compound (Fpmb)$_2$Ir(μ-Cl)$_2$Ir(Fpmb)$_2$

Under a protection of nitrogen, 7.44 g (20.0 mmol) of 1-(2,4-difluorophenyl)-3-methylbenzimidazole iodide, 5.56 g (24 mmol) of silver oxide (Ag$_2$O), 1.77 g (5 mmol) of trihydratediridium chloride and 50 mL of 2-ethoxyethanol were successively added into a 100 ml round bottom flask wrapped by aluminum foil, the mixture was heated and stirred in oil bath at 120° C. for 24 hours. After the mixture was cooled to room temperature, it was concentrated under reduced pressure. The concentrate was then applied to silica gel column chromatography for 2 times using dichloromethane as eluent, and 0.582 g of product in a form of slightly yellow solid was obtained with a yield of 16.3%. The detection data of the product is as follows: $^1$H NMR (400 MHz, CDCl$_3$, ppm): 8.33 (s, 4H), 8.14 (d, 4H), 7.81 (d, 4H), 7.75 (m, 4H), 7.67 (m, 4H), 7.38 (d, 4H), 4.49 (s, 12H).

(3) The Synthesis of Final Products mer-FIr(pmb)$_3$ and fac-FIr(pmb)$_3$

Under a protection of nitrogen, 0.114 g (0.49 mmol) of silver oxide and 0.365 g (0.98 mmol) of 1-(2,4-difluorophenyl)-3-methyl iodide, 0.582 g (0.41 mmol) of bridge compound and 30 mL of 1,2-dichloroethane were successively added into a 50 ml round bottom flask wrapped by aluminum foil, the mixture was heated and stirred in oil bath at 95° C. for 24 hours. After the mixture was cooled to room temperature, it was concentrated under reduced pressure. The concentrate was then applied to silica gel column chromatography for 2 times using dichloromethane as eluent, and 0.74 g of white solid was obtained with the total yield of 98%. The product was applied to silica gel column chromatography using a mixture solution containing ethyl acetate and n-hexane in a volume ratio of 1:4 as eluent, eluted repeatedly to obtain 0.507 g of mer-FIr(pmb)$_3$ with a yield of 67%; the separation residual liquid was applied to silica gel column chromatography using a mixture solution containing ethyl acetate and n-hexane in a volume ratio of 40:60 as eluent, eluted repeatedly to obtain 0.159 g of fac-FIr(pmb)$_3$ with a yield of 21%.

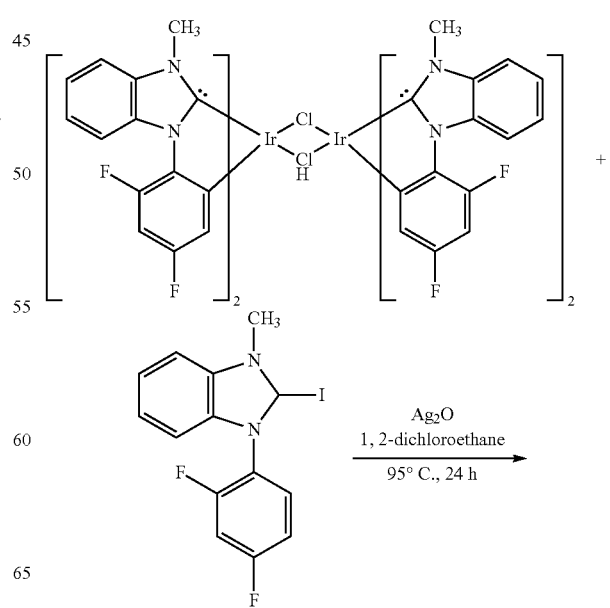

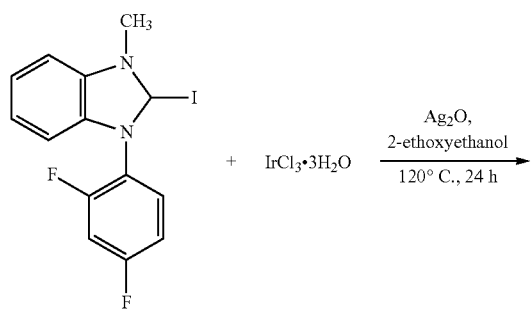

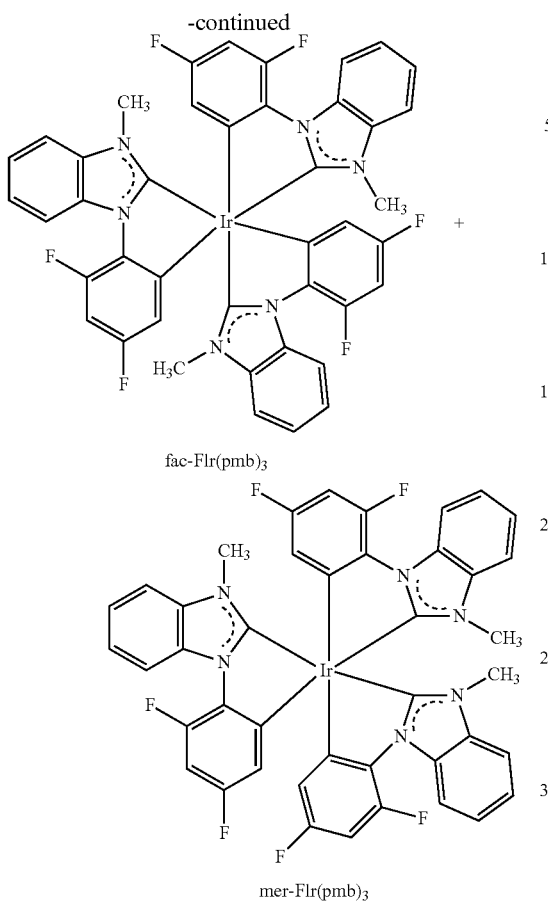

fac-FIr(pmb)₃ mer-FIr(pmb)₃

The detection data of the final product is as follows:

fac-FIr(pmb)₃:

¹H NMR (400 MHz, CDCl₃, ppm): 8.24 (s, 3H), 8.07 (d, 3H), 7.76 (m, 3H), 7.61 (m, 3H), 7.43 (d, 3H), 6.91 (d, 3H), 3.95 (s, 9H).

mer-FIr(pmb)₃:

¹H NMR (400 MHz, CDCl₃, ppm): 8.31 (d, 1H), 8.28 (d, 1H), 8.23 (d, 1H), 7.85 (d, 1H), 7.82 (d, 1H), 7.75 (d, 1H), 7.45-6.51 (m, 12H), 3.96 (s, 3H), 3.87 (s, 3H), 3.75 (s, 3H).

At a temperature of 77 K in 2-methyl-tetrahydrofuran solution (~lemon), fac-FIr(pmb)₃ has a main emission peak at 376 nm in the emission spectrum and a shoulder peak at 396 nm; the mer-FIr(pmb)₃ has a main emission peak at 378 nm and a shoulder peak at 398 nm.

EXAMPLE 2

The synthesis of iridium(III) tris (1-(4',6'-difluorophenyl)-3-ethylbenzimidazolin-2-ylidene-C,C²')

(1) The Synthesis of 1-(2,4-difluorophenyl)-3-methylbenzimidazole iodide

The synthesis of 1-(2,4-difluorophenyl)benzimidazole was identical to that in Example 1.

Under a protection of nitrogen, 1.377 g (8.830 mmol) of ethyl iodide was added to an aluminum foil wrapped 25 mL round bottom flask containing 0.924 g (4.013 mmol) of 1-(2, 4-difluorophenyl)-benzimidazole, and 15 mL of toluene, the system was stirred at 25° C. for 24 hours and white precipitate was generated; the precipitate was washed with 20 mL of toluene and dried to obtain 0.883 g of 1-(2,4-difluorophenyl)-3-methyl iodide in a form of white solid with yield of 57%. The detection data of the product is as follows: ¹H NMR (400 MHz, CDCl₃, ppm): 9.31 (s, 1H), 8.27-8.11 (m, 3H), 7.76-7.64 (m, 4H), 4.43 (m, 2H), 2.45 (m, 3H).

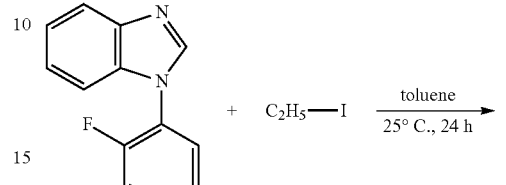

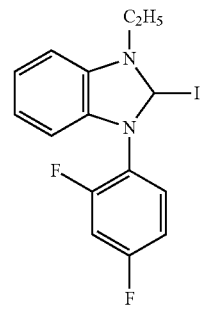

(2) The Synthesis of Bridge Compound (Fpmb)₂Ir(μ-Cl)₂Ir(Fpmb)₂

Under a protection of nitrogen, 7.43 g (20.0 mmol) of 1-(2,4-difluorophenyl)-3-ethyl iodide, 5.56 g (24 mmol) of silver oxide (Ag₂O), 1.77 g (5 mmol) of trihydratediridium chloride and 50 mL of 2-ethoxyethanol were successively added into a 100 ml round bottom flask wrapped by aluminum foil, the mixture was heated and stirred in oil bath at 150° C. for 24 hours. After the mixture was cooled to room temperature, it was concentrated under reduced pressure. The concentrate was then applied to silica gel column chromatography for 2 times using dichloromethane as eluent, and 0.594 g of product in a form of slightly yellow solid was obtained with a yield of 16%. The detection data of the product is as follows: ¹H NMR (400 MHz, CDCl₃, ppm): 8.31 (s, 4H), 8.11 (d, 4H), 7.78 (d, 4H), 7.62 (m, 4H), 7.53 (m, 4H), 7.31 (d, 4H), 4.41 (m, 8H), 2.12 (m, 12H).

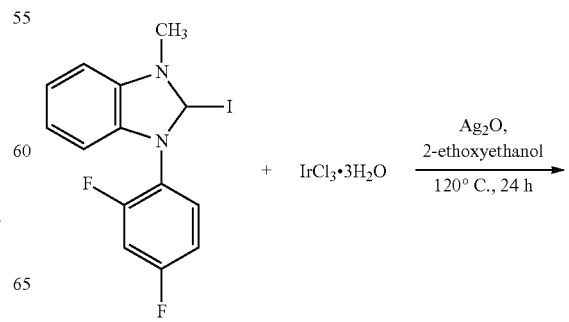

-continued

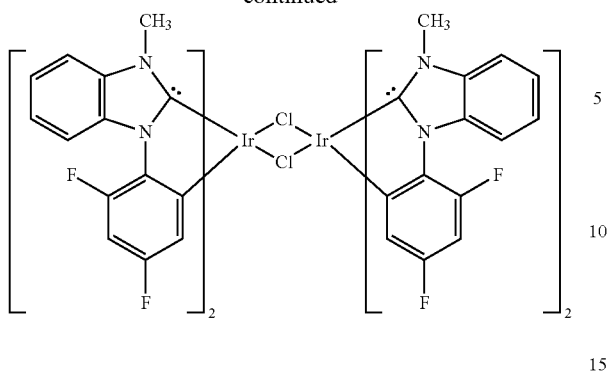

(3) The Synthesis of Final Products mer-FIr(pmb)₃ and fac-FIr(pmb)₃

Under a protection of nitrogen, 0.114 g (0.49 mmol) of silver oxide and 0.378 g (0.98 mmol) of 1-(2,4-difluorophenyl)-3-ethyl iodide, 0.582 g (0.41 mmol) of bridge compound and 30 mL of 1,2-dichloroethane were successively added into a 50 ml round bottom flask wrapped by aluminum foil, the mixture was heated and stirred in oil bath at 90° C. for 24 hours. After the mixture was cooled to room temperature, it was concentrated under reduced pressure. The concentrate was then applied to silica gel column chromatography for 2 times using dichloromethane as eluent, and 0.77 g of white solid was obtained with the total yield of 97%. The product was applied to silica gel column chromatography using a mixture solution containing ethyl acetate and n-hexane in a volume ratio of 20:80 as eluant, eluted repeatedly to obtain 0.522 g of mer-FIr(pmb)₃ with a yield of 66%; the separation residual liquid was applied to silica gel column chromatography using a mixture solution containing ethyl acetate and n-hexane in a volume ratio of 2:3 as eluant, eluted repeatedly to obtain 0.166 g of fac-FIr(pmb)₃ with a yield of 21%.

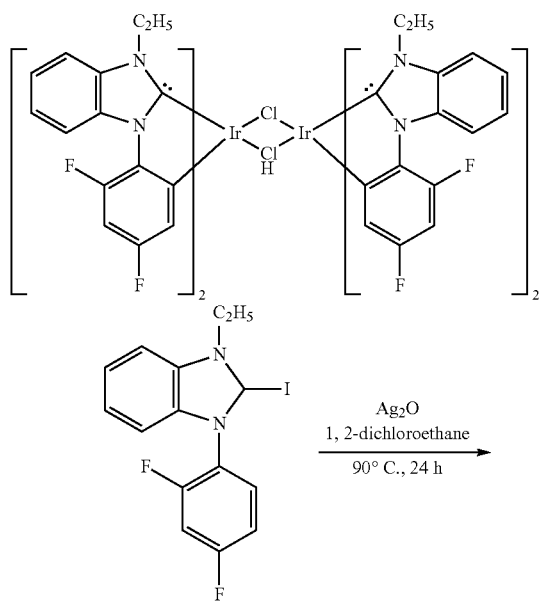

-continued

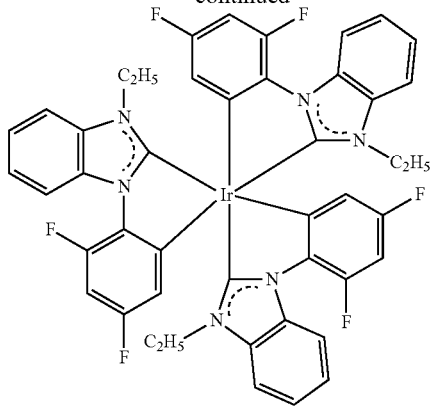

fac-FIr(pmb)₃

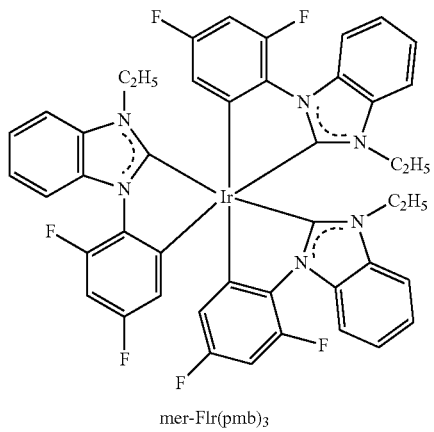

mer-FIr(pmb)₃

The detection data of the final product is as follows:
fac-FIr(pmb)₃:
$^1$H NMR (400 MHz, CDCl₃, ppm): 8.20 (s, 3H), 8.05 (d, 3H), 7.74 (m, 3H), 7.54 (m, 3H), 7.13 (d, 3H), 6.85 (d, 3H), 3.87 (m, 6H), 2.11 (m, 9H).
mer-FIr(pmb)₃:
$^1$H NMR (400 MHz, CDCl₃, ppm): 8.30 (d, 1H), 8.26 (d, 1H), 8.21 (d, 1H), 7.84 (d, 1H), 7.81 (d, 1H), 7.72 (d, 1H), 7.41-6.46 (m, 12H), 3.91-3.72 (m, 6H), 2.19-2.03 (m, 9H).
At a temperature of 77 K in 2-methyl-tetrahydrofuran solution (~10⁻⁵ mol/L), fac-FIr(pmb)₃ has a main emission peak at 377 nm in the emission spectrum and a shoulder peak at 397 nm; the mer-FIr(pmb)₃ has a main emission peak at 379 nm and a shoulder peak at 399 nm.

EXAMPLE 3

The synthesis of iridium(III) tris (1-(4',6'-difluorophenyl)-3-propylbenzimidazolin-2-ylidene-C,C²')

(1) The Synthesis of 1-(2,4-difluorophenyl)-3-propyl benzimidazole iodide

The synthesis of 1-(2,4-difluorophenyl)benzimidazole was identical to that in Example 1.
Under a protection of nitrogen, 1.50 g (8.830 mmol) of propyl iodide was added to an aluminum foil wrapped 25 mL round bottom flask containing 0.924 g (4.013 mmol) of 1-(2, 4-difluorophenyl)-benzimidazole, and 15 mL of toluene, the system was stirred at 45° C. for 24 hours and white precipitate was generated; the precipitate was washed with 20 mL of toluene and dried to obtain 0.932 g of white solid with yield of 58%. The detection data of the product is as follows: ¹H NMR (400 MHz, CDCl₃, ppm): 9.32 (s, 1H), 8.26-8.10 (m, 3H), 7.78-7.66 (m, 4H), 4.43 (m, 2H), 2.60-1.43 (m, 5H).

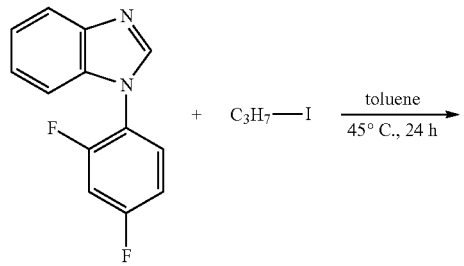

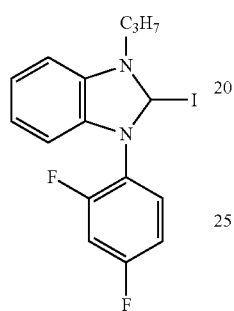

(2) The Synthesis of Bridge Compound (Fpmb)₂Ir(μ-Cl)₂Ir(Fpmb)₂

Under a protection of nitrogen, 8.00 g (20.0 mmol) of 1-(2,4-difluorophenyl)-3-propyl iodide, 5.56 g (24 mmol) of silver oxide (Ag₂O), 1.77 g (5 mmol) of trihydratediridium chloride and 50 mL of 2-ethoxyethanol were successively added into a 100 ml round bottom flask wrapped by aluminum foil, the mixture was heated and stirred in oil bath at 120° C. for 24 hours. After the mixture was cooled to room temperature, it was concentrated under reduced pressure. The concentrate was then applied to silica gel column chromatography for 2 times using dichloromethane as eluent, and 0.609 g of product in a form of slightly yellow solid was obtained with a yield of 15.8%. The detection data of the product is as follows: ¹H NMR (400 MHz, CDCl₃, ppm): 8.25 (s, 4H), 8.08 (d, 4H), 7.72 (d, 4H), 7.56 (m, 4H), 7.43 (m, 4H), 7.26 (d, 4H), 4.34 (m, 8H), 2.51-1.31 (m, 20H).

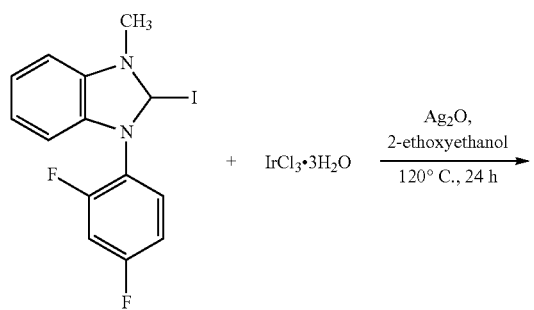

(3) The Synthesis of Final Products mer-FIr(pmb)₃ and fac-FIr(pmb)₃

Under a protection of nitrogen, 0.114 g (0.49 mmol) of silver oxide and 0.392 g (0.98 mmol) of 1-(2,4-difluorophenyl)-3-propyl iodide, 0.582 g (0.41 mmol) of bridge compound and 30 mL of 1,2-dichloroethane were successively added into a 50 ml round bottom flask wrapped by aluminum foil, the mixture was heated and stirred in oil bath at 120° C. for 24 hours. After the mixture was cooled to room temperature, it was concentrated under reduced pressure. The concentrate was then applied to silica gel column chromatography for 2 times using dichloromethane as eluent, and 0.79 g of white solid was obtained with the total yield of 96%. The product was applied to silica gel column chromatography using a mixture solution containing ethyl acetate and n-hexane in a volume ratio of 20:80 as eluent, eluted repeatedly to obtain 0.50 g of mer-FIr(pmb)₃ with a yield of 63%; the separation residual liquid was applied to silica gel column chromatography using a mixture solution containing ethyl acetate and n-hexane in a volume ratio of 2:3 as eluent, eluted repeatedly to obtain 0.174 g of fac-FIr(pmb)₃ with a yield of 22%.

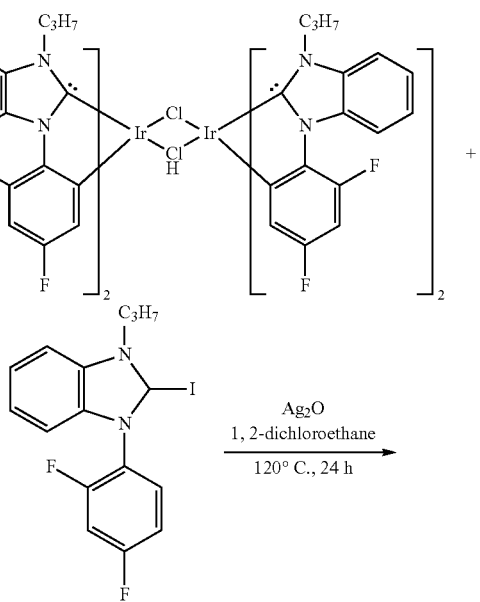

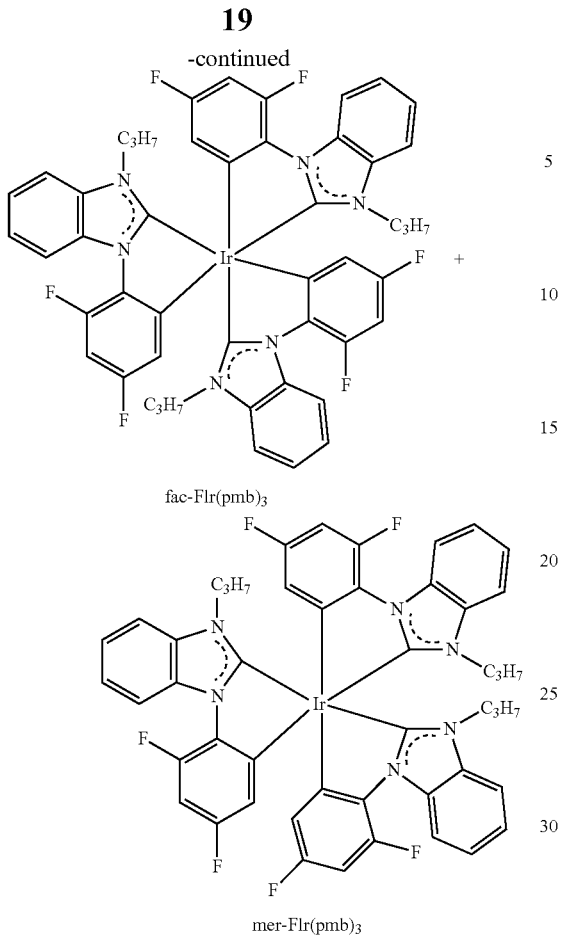

fac-FIr(pmb)₃ mer-FIr(pmb)₃

The detection data of the final product is as follows:

fac-FIr(pmb)₃:

$^1$H NMR (400 MHz, CDCl₃, ppm): 8.13 (s, 3H), 8.01 (d, 3H), 7.71 (m, 3H), 7.45 (m, 3H), 7.11 (d, 3H), 6.83 (d, 3H), 3.81 (m, 6H), 2.13-1.31 (m, 15H).

mer-FIr(pmb)₃:

$^1$H NMR (400 MHz, CDCl₃, ppm): 8.21 (d, 1H), 8.16 (d, 1H), 8.11 (d, 1H), 7.85 (d, 1H), 7.82 (d, 1H), 7.75 (d, 1H), 7.45-6.51 (m, 12H), 3.27-3.20 (m, 6H), 2.19-0.98 (m, 15H).

At a temperature of 77 K in 2-methyl-tetrahydrofuran solution (~10⁻⁵ mol/L), fac-FIr(pmb)₃ has a main emission peak at 377 nm in the emission spectrum and a shoulder peak at 397 nm; the mer-FIr(pmb)₃ has a main emission peak at 379 nm and a shoulder peak at 399 nm.

EXAMPLE 4

The synthesis of iridium(III) tris (1-(4',6'-difluorophenyl)-3-butylbenzimidazolin-2-ylidene-C,C²')

(1) The Synthesis of 1-(2,4-difluorophenyl)-3-butyl benzimidazole iodide

The synthesis of 1-(2,4-difluorophenyl)benzimidazole was identical to that in Example 1.

Under a protection of nitrogen, 1.625 g (8.830 mmol) of butyl iodide was added to an aluminum foil wrapped 25 mL round bottom flask containing 0.924 g (4.013 mmol) of 1-(2,4-difluorophenyl)-benzimidazole, and 15 mL of toluene, the system was stirred at 30° C. for 24 hours and white precipitate was generated; the precipitate was washed with 20 mL of toluene and dried to obtain 0.931 g of white solid with yield of 56%. The detection data of the product is as follows: $^1$H NMR (400 MHz, CDCl₃, ppm): 9.30 (s, 1H), 8.23-8.07 (m, 3H), 7.76-7.64 (m, 3H), 4.44 (m, 2H), 1.23-2.62 (m, 7H).

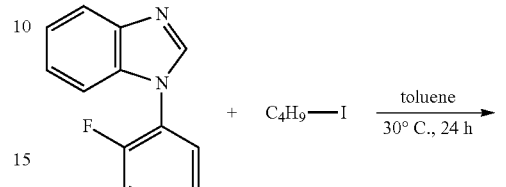

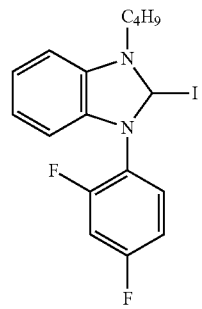

(2) The Synthesis of Bridge Compound (Fpmb)₂Ir(μ-Cl)₂Ir(Fpmb)₂

Under a protection of nitrogen, 8.25 g (20.0 mmol) of 1-(2,4-difluorophenyl)-3-butyl iodide, 5.56 g (24 mmol) of silver oxide (Ag₂O), 1.77 g (5 mmol) of trihydratediridium chloride and 50 mL of 2-ethoxyethanol were successively added into a 100 ml round bottom flask wrapped by aluminum foil, the mixture was heated and stirred in oil bath at 100° C. for 24 hours. After the mixture was cooled to room temperature, it was concentrated under reduced pressure. The concentrate was then applied to silica gel column chromatography for 2 times using dichloromethane as eluent, and 0.627 g of product in a form of slightly yellow solid was obtained with a yield of 15.7%. The detection data of the product is as follows: $^1$H NMR (400 MHz, CDCl₃, ppm): 8.22 (s, 4H), 7.95 (d, 4H), 7.70 (d, 4H), 7.46 (m, 4H), 7.34 (m, 4H), 7.21 (d, 4H), 4.25 (m, 8H), 2.42-1.21 (m, 28H).

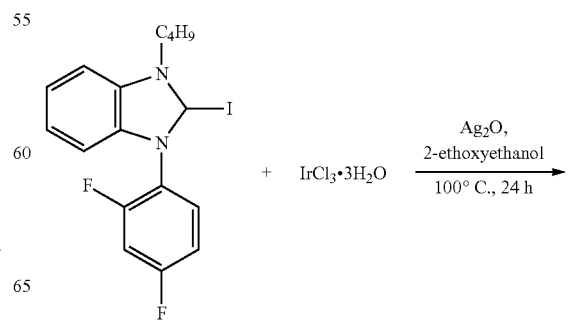

-continued

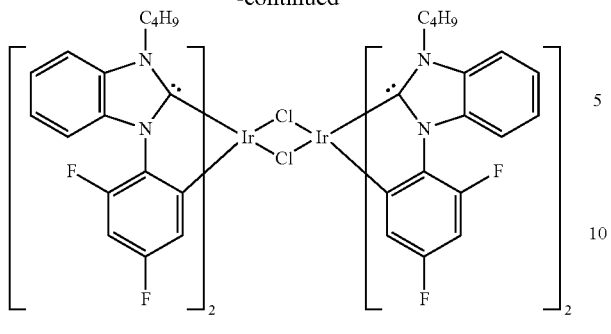

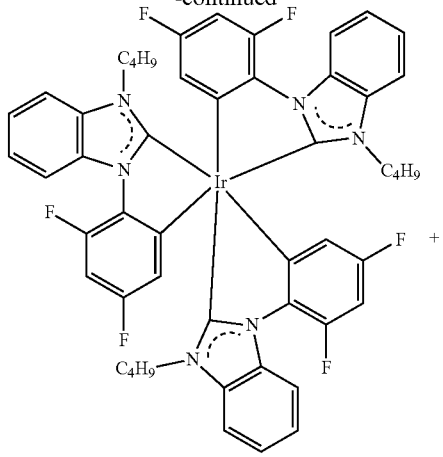

fac-FIr(pmb)₃

(3) The Synthesis of Final Products mer-FIr(pmb)₃ and fac-FIr(pmb)₃

Under a protection of nitrogen, 0.114 g (0.49 mmol) of silver oxide and 0.406 g (0.98 mmol) of 1-(2,4-difluorophenyl)-3-butyl iodide, 0.582 g (0.41 mmol) of bridge compound and 30 mL of 1,2-dichloroethane were successively added into a 50 ml round bottom flask wrapped by aluminum foil, the mixture was heated and stirred in oil bath at 150° C. for 24 hours. After the mixture was cooled to room temperature, it was concentrated under reduced pressure. The concentrate was then applied to silica gel column chromatography for 2 times using dichloromethane as eluent, and 0.84 g of white solid was obtained with the total yield of 98%. The product was applied to silica gel column chromatography using a mixture solution containing ethyl acetate and n-hexane in a volume ratio of 20:80 as eluant, eluted repeatedly to obtain 0.551 g of mer-FIr(pmb)₃ with a yield of 64%; the separation residual liquid was applied to silica gel column chromatography using a mixture solution containing ethyl acetate and n-hexane in a volume ratio of 40:60 as eluant, eluted repeatedly to obtain 0.181 g of fac-FIr(pmb)₃ with a yield of 21%.

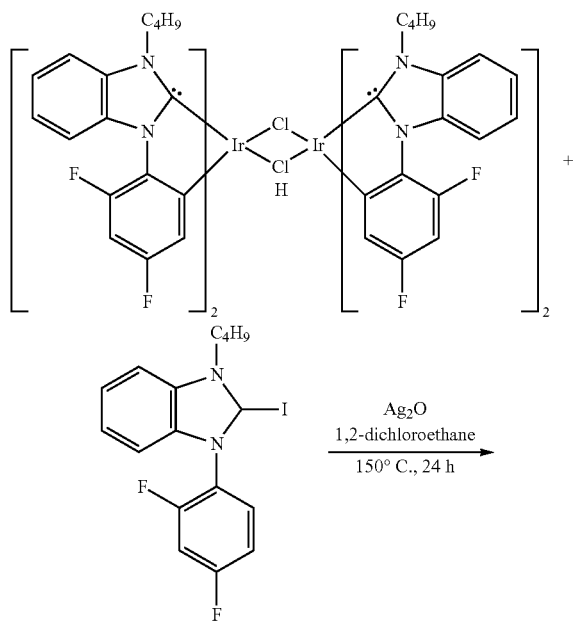

mer-FIr(pmb)₃

The detection data of the final product is as follows:

fac-FIr(pmb)₃:
¹H NMR (400 MHz, CDCl₃, ppm): 8.11 (s, 3H), 7.96 (d, 3H), 7.68 (m, 3H), 7.36 (m, 3H), 7.03 (d, 3H), 6.78 (d, 3H), 3.71 (m, 6H), 2.11-0.98 (m, 21H).

mer-FIr(pmb)₃:
¹H NMR (400 MHz, CDCl₃, ppm): 8.21 (d, 1H), 8.14 (d, 1H), 8.02 (d, 1H), 7.81 (d, 1H), 7.77 (d, 1H), 7.67 (d, 1H), 7.44-6.53 (m, 12H), 3.27-3.11 (m, 6H), 2.19-0.97 (m, 21H).

At a temperature of 77 K in 2-methyl-tetrahydrofuran solution (~10⁻⁵ mol/L), fac-FIr(pmb)₃ has a main emission peak at 378 nm in the emission spectrum and a shoulder peak at 398 nm; the mer-FIr(pmb)₃ has a main emission peak at 379 nm and a shoulder peak at 399 nm.

EXAMPLE 5

The synthesis of iridium(III) tris (1-(4',6'-difluorophenyl)-3-pentylbenzimidazolin-2-ylidene-C,C²')

(1) The Synthesis of 1-(2,4-difluorophenyl)-3-pentylchroman iodide

The synthesis of 1-(2,4-difluorophenyl)benzimidazole was identical to that in Example 1.

Under a protection of nitrogen, 1.748 g (8.830 mmol) of iodopentane was added to an aluminum foil wrapped 25 mL round bottom flask containing 0.924 g (4.013 mmol) of 1-(2,4-difluorophenyl)-benzimidazole, and 15 mL of toluene, the system was stirred at 40° C. for 24 hours and white precipitate was generated; the precipitate was washed with 20 mL of toluene and dried to obtain 0.882 g of white solid with yield of 59%. The detection data of the product is as follows: $^1$H NMR (400 MHz, CDCl$_3$, ppm): 9.30 (s, 1H), 8.21-7.97 (m, 3H), 7.75-7.63 (m, 3H), 4.43 (m, 3H), 1.16-2.45 (m, 9H).

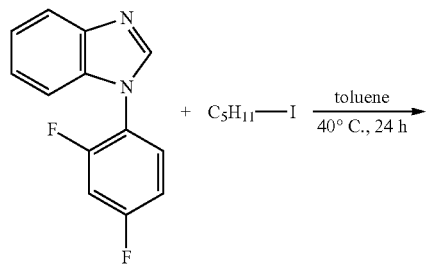

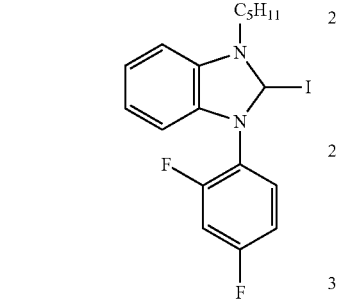

(2) The Synthesis of Bridge Compound (Fpmb)$_2$(μ-Cl)$_2$Ir(Fpmb)$_2$

Under a protection of nitrogen, 8.27 g (20.0 mmol) of 1-(2,4-difluorophenyl)-3-pentylchroman iodide, 5.56 g (24 mmol) of silver oxide (Ag$_2$O), 1.77 g (5 mmol) of trihydrate-diridium chloride and 50 mL of 2-ethoxyethanol were successively added into a 100 ml round bottom flask wrapped by aluminum foil, the mixture was heated and stirred in oil bath at 130° C. for 24 hours. After the mixture was cooled to room temperature, it was concentrated under reduced pressure. The concentrate was then applied to silica gel column chromatography for 2 times using dichloromethane as eluent, and 0.64 g of product in a form of slightly yellow solid was obtained with a yield of 15.5%. The detection data of the product is as follows: $^1$H NMR (400 MHz, CDCl$_3$, ppm): 8.18 (s, 4H), 7.91 (d, 4H), 7.68 (d, 4H), 7.43 (m, 4H), 7.30 (m, 4H), 7.14 (d, 4H), 4.21 (m, 8H), 2.38-0.97 (m, 36H).

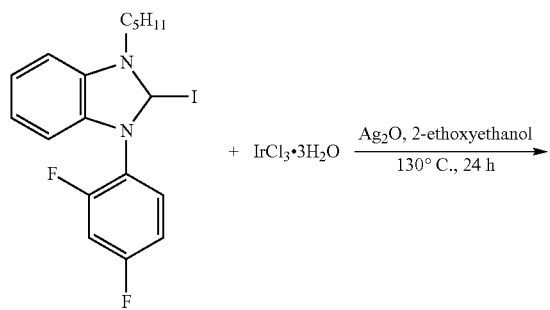

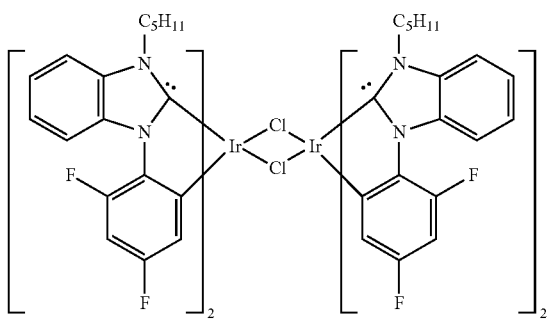

(3) The Synthesis of Final Products mer-FIr(pmb)$_3$ and fac-FIr(pmb)$_3$

Under a protection of nitrogen, 0.114 g (0.49 mmol) of silver oxide and 0.42 g (0.98 mmol) of 1-(2,4-difluorophenyl)-3-pentylchroman iodide, 0.582 g (0.41 mmol) of bridge compound and 30 mL of 1,2-dichloroethane were successively added into a 50 ml round bottom flask wrapped by aluminum foil, the mixture was heated and stirred in oil bath at 95° C. for 24 hours. After the mixture was cooled to room temperature, it was concentrated under reduced pressure. The concentrate was then applied to silica gel column chromatography for 2 times using dichloromethane as eluent, and 0.85 g of white solid was obtained with the total yield of 95%. The product was applied to silica gel column chromatography using a mixture solution containing ethyl acetate and n-hexane in a volume ratio of 20:80 as eluent, eluted repeatedly to obtain 0.564 g of mer-FIr(pmb)$_3$ with a yield of 63%; the separation residual liquid was applied to silica gel column chromatography using a mixture solution containing ethyl acetate and n-hexane in a volume ratio of 2:3 as eluent, eluted repeatedly to obtain 0.162 g of fac-FIr(pmb)$_3$ with a yield of 19%.

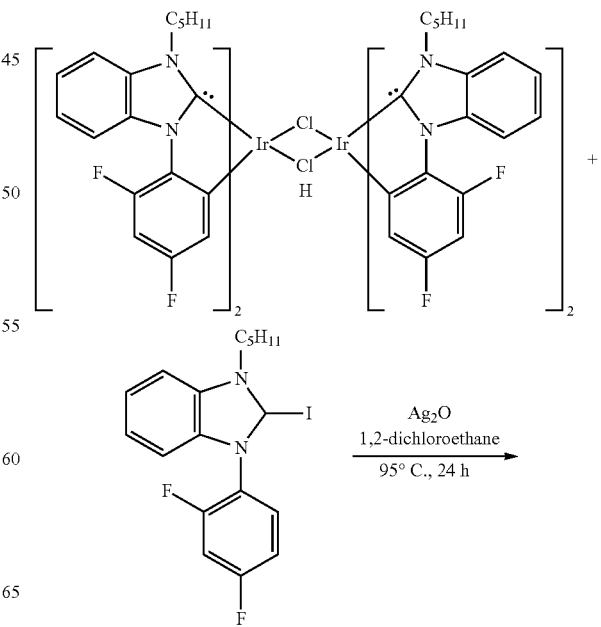

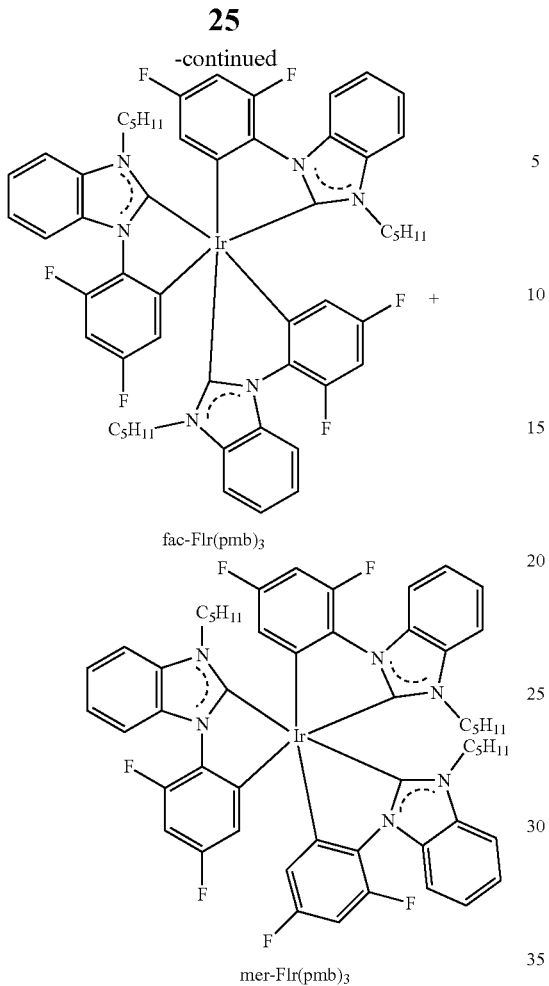

fac-FIr(pmb)₃ mer-FIr(pmb)₃

The detection data of the final product is as follows:
fac-FIr(pmb)₃:
¹H NMR (400 MHz, CDCl₃, ppm): 8.11 (s, 3H), 7.94 (d, 3H), 7.68 (m, 3H), 7.23 (m, 3H), 6.97 (d, 3H), 6.65 (d, 3H), 3.70 (m, 6H), 2.13-0.98 (m, 27H).
mer-FIr(pmb)₃:
¹H NMR (400 MHz, CDCl₃, ppm): 8.21 (d, 1H), 8.13 (d, 1H), 8.01 (d, 1H), 7.80 (d, 1H), 7.71 (d, 1H), 7.61 (d, 1H), 7.45-6.51 (m, 12H), 3.20-3.11 (m, 6H), 2.19-0.98 (m, 27H).

At a temperature of 77 K in 2-methyl-tetrahydrofuran solution (~10⁻⁵ mol/L), fac-FIr(pmb)₃ has a main emission peak at 379 nm in the emission spectrum and a shoulder peak at 399 nm; the mer-FIr(pmb)₃ has a main emission peak at 380 nm and a shoulder peak at 400 nm.

EXAMPLE 6

The synthesis of iridium(III) tris (1-(4',6'-difluorophenyl)-3-hexylbenzimidazolin-2-ylidene-C,C²')

(1) The Synthesis of 1-(2,4-difluorophenyl)-3-methylbenzimidazole iodide

The synthesis of 1-(2,4-difluorophenyl)benzimidazole was identical to that in Example 1.

Under a protection of nitrogen, 1.871 g (8.830 mmol) of iodohexane was added to an aluminum foil wrapped 25 mL round bottom flask containing 0.924 g (4.013 mmol) of 1-(2, 4-difluorophenyl)-benzimidazole, and 15 mL of toluene, the system was stirred at 30° C. for 24 hours and white precipitate was generated; the precipitate was washed with 20 mL of toluene and dried to obtain 0.882 g white solid with yield of 59%. The detection data of the product is as follows: ¹H NMR (400 MHz, CDCl₃, ppm): 9.31 (s, 1H), 8.21-7.96 (m, 3H), 7.72-7.61 (m, 3H), 4.41 (m, 3H), 1.12-2.36 (m, 11H).

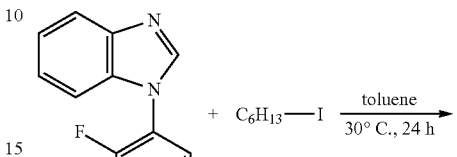

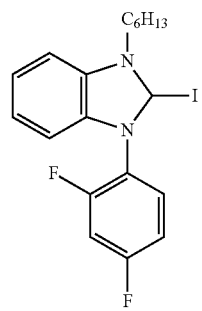

(2) The Synthesis of Bridge Compound (Fpmb)₂Ir(μ-Cl)₂Ir(Fpmb)₂

Under a protection of nitrogen, 8.85 g (20.0 mmol) of 1-(2,4-difluorophenyl)-3-hexylbenzotriazole iodide, 5.56 g (24 mmol) of silver oxide (Ag₂O), 1.77 g (5 mmol) of trihydratediridium chloride and 50 mL of 2-ethoxyethanol were successively added into a 100 ml round bottom flask wrapped by aluminum foil, the mixture was heated and stirred in oil bath at 120° C. for 24 hours. After the mixture was cooled to room temperature, it was concentrated under reduced pressure. The concentrate was then applied to silica gel column chromatography for 2 times using dichloromethane as eluent, and 0.662 g of product in a form of slightly yellow solid was obtained with a yield of 15.8%. The detection data of the product is as follows: ¹H NMR (400 MHz, CDCl₃, ppm): 8.17 (s, 4H), 7.84 (d, 4H), 7.55 (d, 4H), 7.36 (m, 4H), 7.23 (m, 4H), 7.05 (d, 4H), 4.13 (m, 8H), 2.21-0.98 (m, 44H).

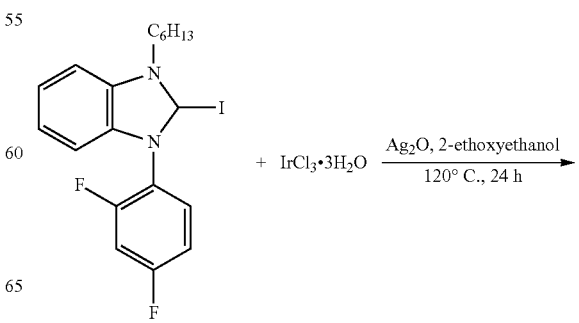

-continued

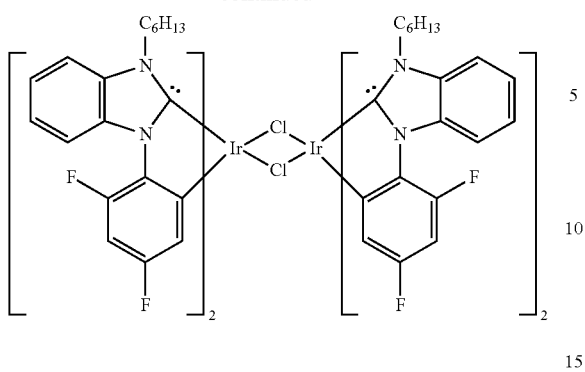

(3) The Synthesis of Final Products mer-FIr(pmb)₃ and fac-FIr(pmb)₃

Under a protection of nitrogen, 0.114 g (0.49 mmol) of silver oxide and 0.433 g (0.98 mmol) of 1-(2,4-difluorophenyl)-3-hexylbenzotriazole iodide, 0.582 g (0.41 mmol) of bridge compound and 30 mL of 1,2-dichloroethane were successively added into a 50 ml round bottom flask wrapped by aluminum foil, the mixture was heated and stirred in oil bath at 100° C. for 24 hours. After the mixture was cooled to room temperature, it was concentrated under reduced pressure. The concentrate was then applied to silica gel column chromatography for 2 times using dichloromethane as eluent, and 0.864 g of white solid was obtained with the total yield of 93%. The product was applied to silica gel column chromatography using a mixture solution containing ethyl acetate and n-hexane in a volume ratio of 20:80 as eluant, eluted repeatedly to obtain 0.604 g of mer-FIr(pmb)₃ with a yield of 65%; the separation residual liquid was applied to silica gel column chromatography using a mixture solution containing ethyl acetate and n-hexane in a volume ratio of 2:3 as eluant, eluted repeatedly to obtain 0.186 g of fac-FIr(pmb)₃ with a yield of 20%.

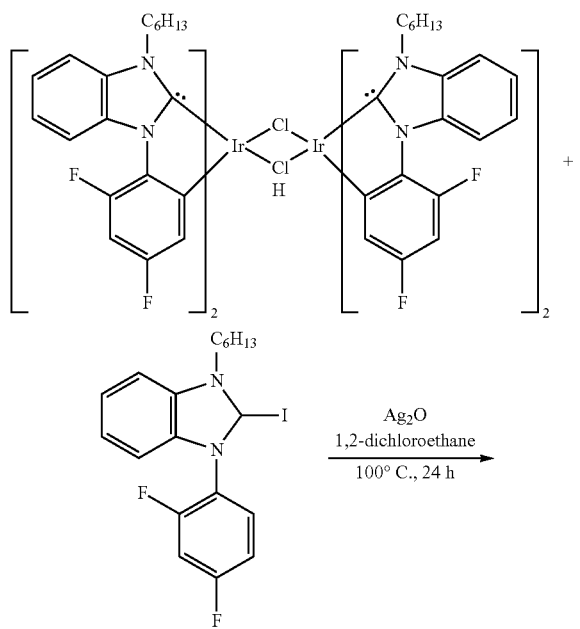

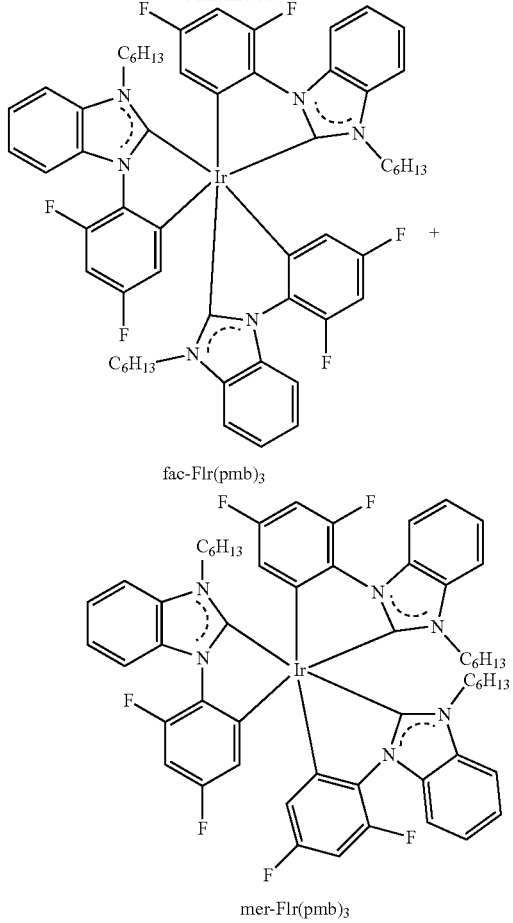

fac-FIr(pmb)₃ mer-FIr(pmb)₃

The detection data of the final product is as follows:

fac-FIr(pmb)₃:
$^1$H NMR (400 MHz, CDCl₃, ppm): 8.10 (s, 3H), 7.88 (d, 3H), 7.70 (m, 3H), 7.24 (m, 3H), 6.87 (d, 3H), 6.65 (d, 3H), 3.71 (m, 6H), 2.15-0.98 (m, 33H).

mer-FIr(pmb)₃:
$^1$H NMR (400 MHz, CDCl₃, ppm): 8.19 (d, 1H), 8.17 (d, 1H), 8.08 (d, 1H), 7.85 (d, 1H), 7.81 (d, 1H), 7.68 (d, 1H), 7.44-6.52 (m, 12H), 3.20-3.12 (m, 6H), 2.16-0.98 (m, 33H).

At a temperature of 77 K in 2-methyl-tetrahydrofuran solution (~$10^{-5}$ mol/L), fac-FIr(pmb)₃ has a main emission peak at 379 nm in the emission spectrum and a shoulder peak at 399 nm; the mer-FIr(pmb)₃ has a main emission peak at 381 nm and a shoulder peak at 401 nm.

EXAMPLE 7

The synthesis of iridium(III) tris (1-(4',6'-difluorophenyl)-3-heptylbenzimidazolin-2-ylidene-C,C²')

(1) The Synthesis of 1-(2,4-difluorophenyl)-3-heptylphenoxy iodide

The synthesis of 1-(2,4-difluorophenyl)benzimidazole was identical to that in Example 1.

Under a protection of nitrogen, 1.994 g (8.830 mmol) of iodoheptane was added to an aluminum foil wrapped 25 mL round bottom flask containing 0.924 g (4.013 mmol) of 1-(2,4-difluorophenyl)-benzimidazole, and 15 mL of toluene, the system was stirred at 30° C. for 24 hours and white precipitate was generated; the precipitate was washed with 20 mL of toluene and dried to obtain 0.882 g of white solid with yield of 59%. The detection data of the product is as follows: $^1$H NMR (400 MHz, CDCl$_3$, ppm): 9.29 (s, 1H), 8.21-7.94 (m, 3H), 7.71-7.60 (m, 3H), 4.40 (m, 3H), 1.08-2.24 (m, 13H).

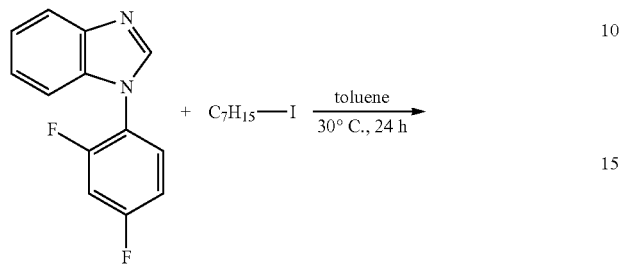

(2) The Synthesis of Bridge Compound (Fpmb)$_2$Ir(μ-Cl)$_2$Ir(Fpmb)$_2$

Under a protection of nitrogen, 9.13 g (20.0 mmol) of 1-(2,4-difluorophenyl)-3-heptylphenoxy iodide, 5.56 g (24 mmol) of silver oxide (Ag$_2$O), 1.77 g (5 mmol) of trihydrate-diridium chloride and 50 mL of 2-ethoxyethanol were successively added into a 100 ml round bottom flask wrapped by aluminum foil, the mixture was heated and stirred in oil bath at 120° C. for 24 hours. After the mixture was cooled to room temperature, it was concentrated under reduced pressure. The concentrate was then applied to silica gel column chromatography for 2 times using dichloromethane as eluent, and 0.666 g of product in a form of slightly yellow solid was obtained with a yield of 15.1%. The detection data of the product is as follows: $^1$H NMR (400 MHz, CDCl$_3$, ppm): 8.15 (s, 4H), 7.81 (d, 4H), 7.54 (d, 4H), 7.31 (m, 4H), 7.22 (m, 4H), 6.98 (d, 4H), 4.01 (m, 8H), 2.14-0.89 (m, 52H).

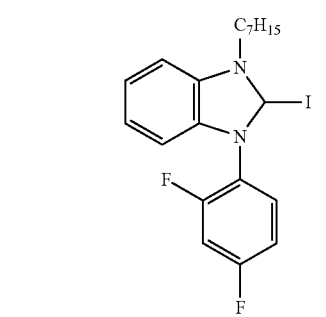

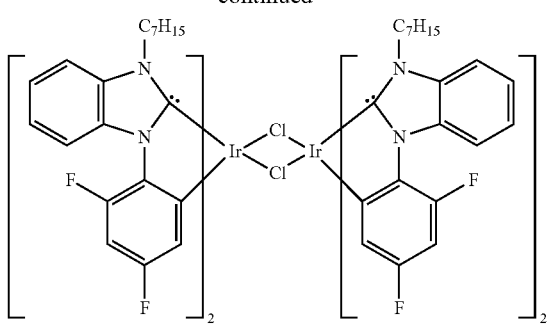

(3) The Synthesis of Final Products mer-FIr(pmb)$_3$ andfac-FIr(pmb)$_3$

Under a protection of nitrogen, 0.114 g (0.49 mmol) of silver oxide and 0.447 g (0.98 mmol) of 1-(2,4-difluorophenyl)-3-heptylphenoxy iodide, 0.582 g (0.41 mmol) of bridge compound and 30 mL of 1,2-dichloroethane were successively added into a 50 ml round bottom flask wrapped by aluminum foil, the mixture was heated and stirred in oil bath at 140° C. for 24 hours. After the mixture was cooled to room temperature, it was concentrated under reduced pressure. The concentrate was then applied to silica gel column chromatography for 2 times using dichloromethane as eluent, and 0.887 g of white solid was obtained with the total yield of 92%. The product was applied to silica gel column chromatography using a mixture solution containing ethyl acetate and n-hexane in a volume ratio of 20:80 as eluant, eluted repeatedly to obtain 0.578 g of mer-FIr(pmb)$_3$ with a yield of 60%; the separation residual liquid was applied to silica gel column chromatography using a mixture solution containing ethyl acetate and n-hexane in a volume ratio of 2:3 as eluant, eluted repeatedly to obtain 0.202 g of fac-FIr(pmb)$_3$ with a yield of 21%.

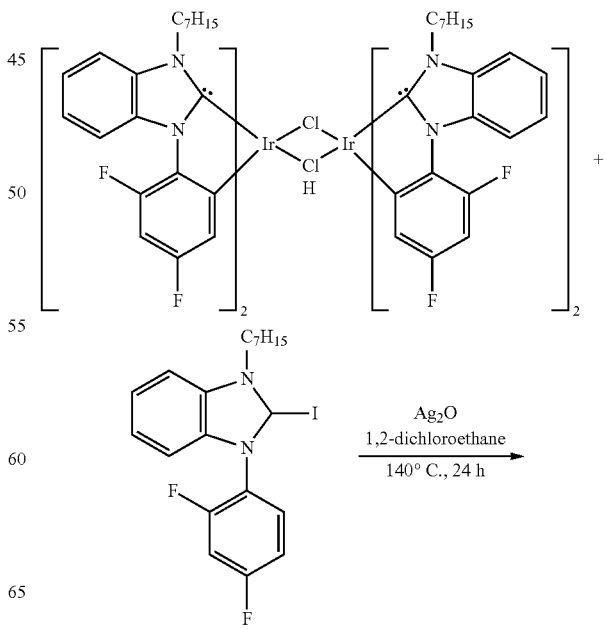

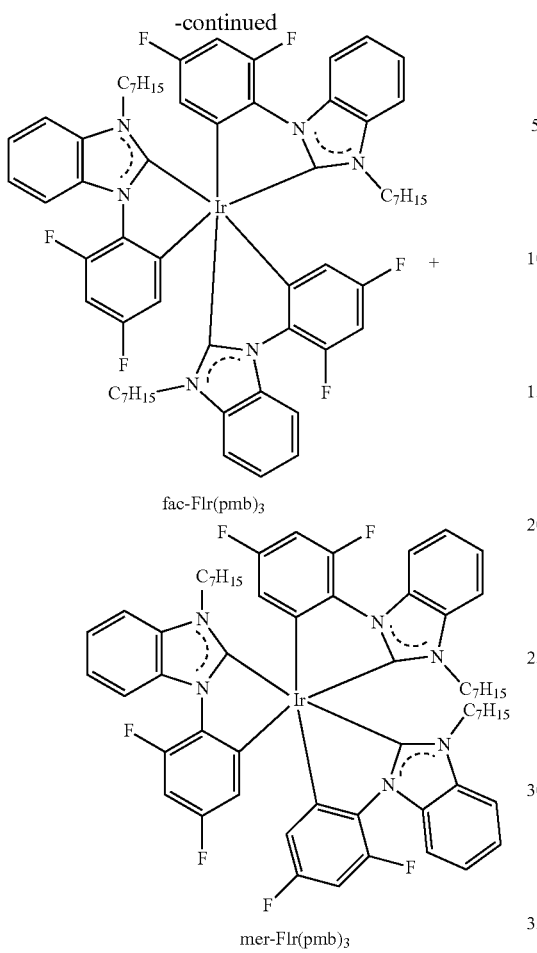

fac-FIr(pmb)₃ mer-FIr(pmb)₃

The detection data of the final product is as follows:
fac-FIr(pmb)₃:
$^1$H NMR (400 MHz, CDCl₃, ppm): 8.09 (s, 3H), 7.87 (d, 3H), 7.66 (m, 3H), 7.25 (m, 3H), 6.86 (d, 3H), 6.67 (d, 3H), 3.73 (m, 6H), 2.14-0.97 (m, 39H).

(B) mer-FIr(pmb)₃:
$^1$H NMR (400 MHz, CDCl₃, ppm): 8.15 (d, 1H), 8.08 (d, 1H), 7.97 (d, 1H), 7.76 (d, 1H), 7.71 (d, 1H), 7.62 (d, 1H), 7.45-6.51 (m, 12H), 3.20-3.01 (m, 6H), 2.11-0.98 (m, 39H).

At a temperature of 77 K in 2-methyl-tetrahydrofuran solution (~10⁻⁵ mol/L), fac-FIr(pmb)₃ has a main emission peak at 379 nm in the emission spectrum and a shoulder peak at 399 nm; the mer-FIr(pmb)₃ has a main emission peak at 382 nm and a shoulder peak at 402 nm.

EXAMPLE 8

The synthesis of iridium(III) tris (1-(4',6'-difluorophenyl)-3-octylbenzimidazolin-2-ylidene-C,C²')

(1) The Synthesis of 1-(2,4-difluorophenyl)-3-octyl benzimidazol iodide

The synthesis of 1-(2,4-difluorophenyl)benzimidazole was identical to that in Example 1.

Under a protection of nitrogen, 2.117 g (8.830 mmol) of iodooctane was added to an aluminum foil wrapped 25 mL round bottom flask containing 0.924 g (4.013 mmol) of 1-(2,4-difluorophenyl)-benzimidazole, and 15 mL of toluene, the system was stirred at 30° C. for 24 hours and white precipitate was generated; the precipitate was washed with 20 mL of toluene and dried to obtain 0.882 g of white solid with yield of 59%. The detection data of the product is as follows: $^1$H NMR (400 MHz, CDCl₃, ppm): 9.28 (s, 1H), 8.17-7.90 (m, 3H), 7.71-7.62 (m, 3H), 4.39 (s, 3H), 1.05-2.18 (m, 15H).

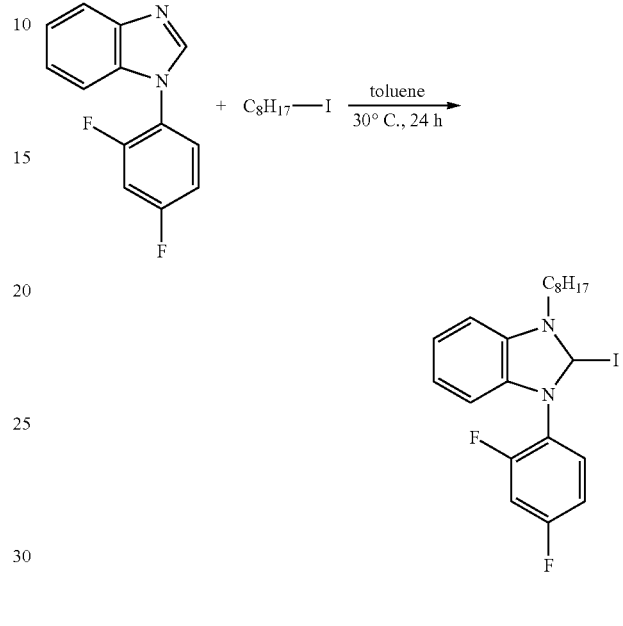

(2) The Synthesis of Bridge Compound (Fpmb)₂Ir(μ-Cl)₂Ir(Fpmb)₂

Under a protection of nitrogen, 9.41 g (20.0 mmol) of 1-(2,4-difluorophenyl)-3-octyl iodide, 5.56 g (24 mmol) of silver oxide (Ag₂O), 1.77 g (5 mmol) of trihydratediridium chloride and 50 mL of 2-ethoxyethanol were successively added into a 100 ml round bottom flask wrapped by aluminum foil, the mixture was heated and stirred in oil bath at 120° C. for 24 hours. After the mixture was cooled to room temperature, it was concentrated under reduced pressure. The concentrate was then applied to silica gel column chromatography for 2 times using dichloromethane as eluent, and 0.692 g of product in a form of slightly yellow solid was obtained with a yield of 15.2%. The detection data of the product is as follows: $^1$H NMR (400 MHz, CDCl₃, ppm): 8.14 (s, 4H), 7.76 (d, 4H), 7.51 (d, 4H), 7.31 (m, 4H), 7.21 (m, 4H), 6.87 (d, 4H), 3.91 (m, 8H), 2.12-0.89 (m, 60H).

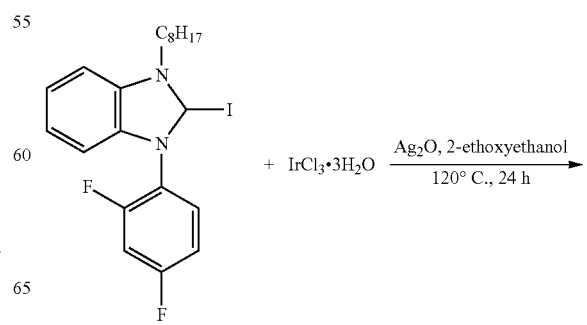

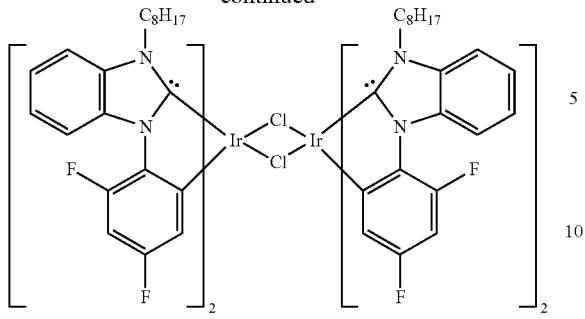

(3) The Synthesis of Final Products mer-FIr(pmb)₃ and fac-FIr(pmb)₃

Under a protection of nitrogen, 0.114 g (0.49 mmol) of silver oxide and 0.461 g (0.98 mmol) of 1-(2,4-difluorophenyl)-3-octyl iodide, 0.582 g (0.41 mmol) of bridge compound and 30 mL of 1,2-dichloroethane were successively added into a 50 ml round bottom flask wrapped by aluminum foil, the mixture was heated and stirred in oil bath at 95° C. for 24 hours. After the mixture was cooled to room temperature, it was concentrated under reduced pressure. The concentrate was then applied to silica gel column chromatography for 2 times using dichloromethane as eluent, and 0.908 g of white solid was obtained with the total yield of 91%. The product was applied to silica gel column chromatography using a mixture solution containing ethyl acetate and n-hexane in a volume ratio of 20:80 as eluant, eluted repeatedly to obtain 0.589 g of mer-FIr(pmb)₃ with a yield of 59%; the separation residual liquid was applied to silica gel column chromatography using a mixture solution containing ethyl acetate and n-hexane in a volume ratio of 2:3 as eluant, eluted repeatedly to obtain 0.18 g of fac-FIr(pmb)₃ with a yield of 18%.

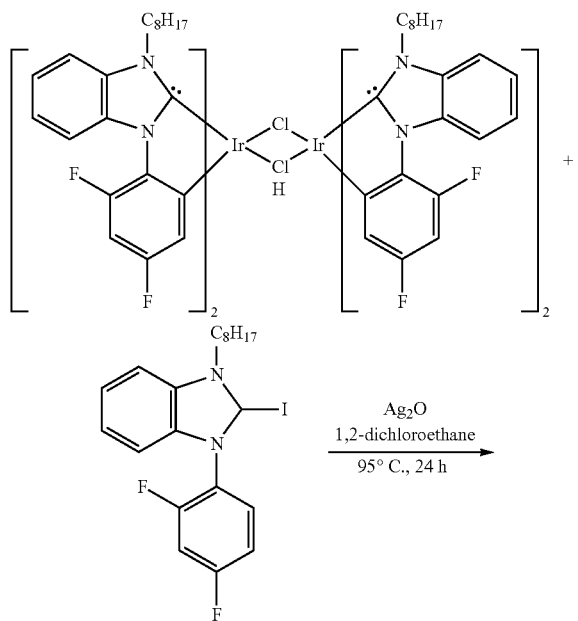

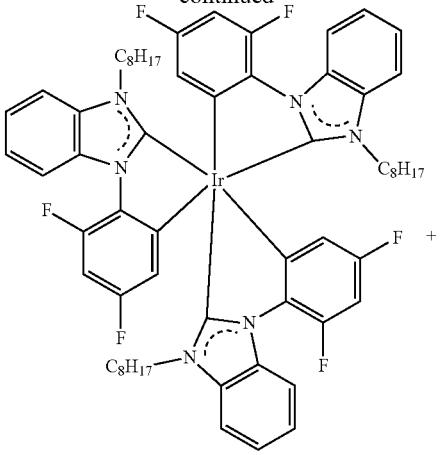

The detection data of the final product is as follows:

fac-FIr(pmb)₃:
¹H NMR (400 MHz, CDCl₃, ppm): 8.02 (s, 3H), 7.86 (d, 3H), 7.64 (m, 3H), 7.25 (m, 3H), 6.84 (d, 3H), 6.61 (d, 3H), 3.51 (m, 6H), 2.15-0.96 (m, 45H).

mer-FIr(pmb)₃:
¹H NMR (400 MHz, CDCl₃, ppm): 8.15 (d, 1H), 8.13 (d, 1H), 8.05 (d, 1H), 7.75 (d, 1H), 7.67 (d, 1H), 7.58 (d, 1H), 7.41-6.53 (m, 12H), 3.20-3.02 (m, 6H), 2.19-0.96 (m, 45H).

At a temperature of 77 K in 2-methyl-tetrahydrofuran solution (~10⁻⁵ mol/L), fac-FIr(pmb)₃ has a main emission peak at 380 nm in the emission spectrum and a shoulder peak at 400 the mer-FIr(pmb)₃ has a main emission peak at 382 m and a shoulder peak at 402 nm.

Figure 3:
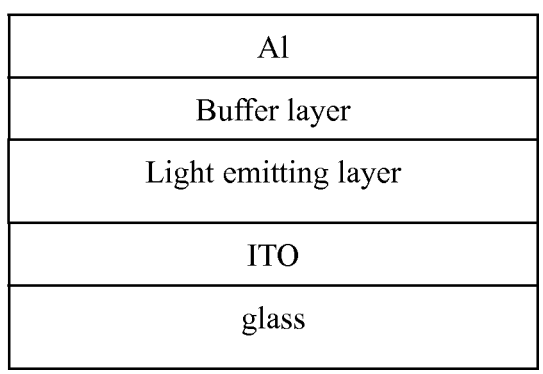
FIG. 3 is a schematic view of the organic electroluminescent device in Example 8.

(4) The Structure of an Organic Electroluminescent Element is Shown in FIG. 3 Using FIr(pmb)₃ of the Present Embodiment as a Doped Object in the Light-Emitting Layer The element includes ITO/FIr(pmb)₃/LiF/Al, i.e. it is formed by depositing indium tin oxide (ITO) on a glass substrate with a sheet resistance of 10-20 Ω/sq as a transparent anode; preparing a FIr(pmb)₃ of the present embodiment on the ITO as a light-emitting layer by spin coating technique; and then vacuum depositing LiF on the light-emitting layer as a buffer layer; and finally depositing metal Al on the buffer layer using vacuum coating technology as a cathode of the element. Since the light-emitting layer containing an iridium-containing organic electroluminescent material has high internal quantum efficiency and the electroluminescent efficiency, the electroluminescent element has a high energy conversion efficiency and luminous efficiency.

Although the invention has been described in language specific to structural features and/or methodological acts, it is to be understood that the invention defined in the appended claims is not necessarily limited to the specific features or acts described. Rather, the specific features and acts are disclosed as sample forms of implementing the claimed invention.

What is claimed is:

1. A preparation method of an iridium containing organic electroluminescent material, comprising the following steps:

step one: preparing a compound A represented by the following formula:

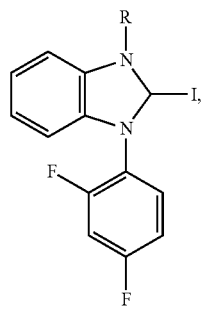

wherein R is $C_1$-$C_8$ alkyl;

step two: performing reaction between compound A and trihydrate iridium trichloride in a solvent under an anaerobic condition in presence of $Ag_2O$ catalyst to obtain a bridge compound B; the reaction equation being:

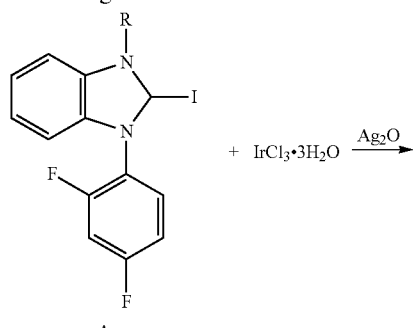

and step three: performing ligands interchange reaction between bridge compound B and compound A in a solvent under an anaerobic condition in presence of $Ag_2O$ catalyst to obtain the compound I; the reaction equation being:

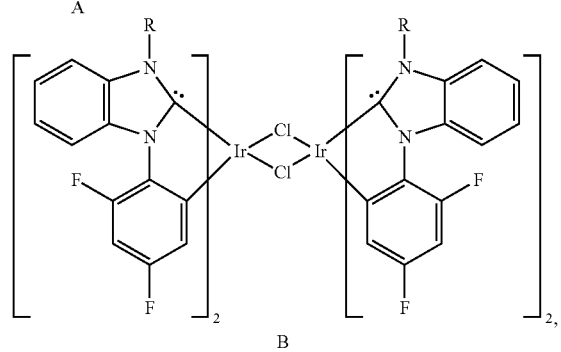

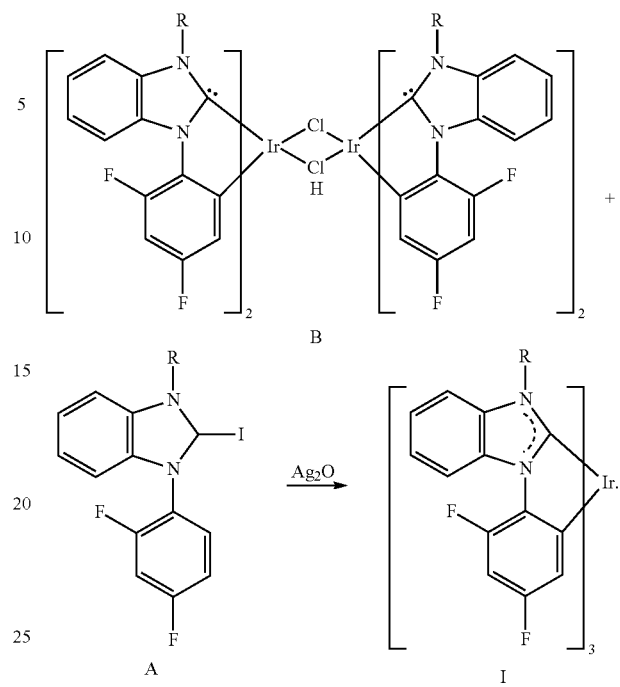

2. The preparation method according to claim 1, wherein the solvent in step two is 2-ethoxyethanol, and the reaction temperature is from 100° C. to 150° C.; the solvent in step three is 1,2-dichloroethane, and the reaction temperature is from 90° C. to 150° C.

3. The preparation method according to claim 1, wherein the step two further comprises separation and purification steps: an obtained mixture after the reaction between compound A and iridium trichloride trihydrate is firstly concentrated under reduced pressure; the concentrate is then applied to silica gel column chromatography for 2 to 3 times using dichloromethane as eluent, and the purified compound B is obtained.

4. The preparation method according to claim 1, wherein the step three further comprises separation and purification steps:

firstly, the reaction product containing the compound I is concentrated under reduced pressure to obtain a concentrated product containing compound I;

then, the concentrated product is applied to silica gel column chromatography using dichloromethane as eluent to obtain a solid mixture containing isomer II and isomer III;

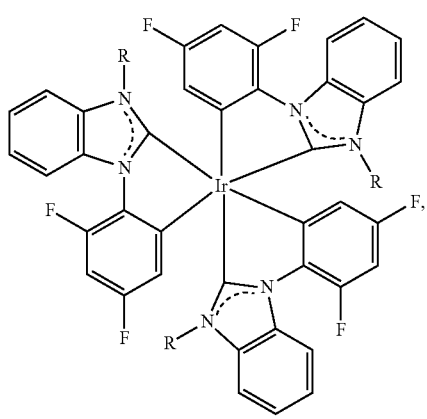

-continued

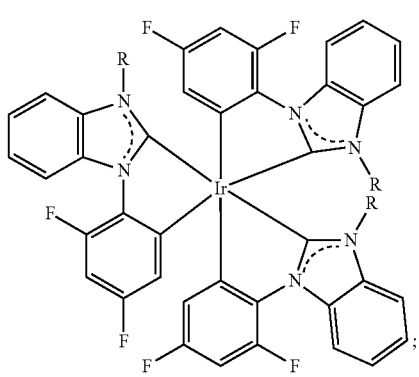

III the solid mixture is applied to silica gel column chromatography using a mixture solution containing ethyl acetate and n-hexane in a volume ratio of 1:4 as eluant to obtain a purified compound III and separation residual liquid;

finally, the separation residual liquid is applied to silica gel column chromatography using a mixture solution containing ethyl acetate and n-hexane in a volume ratio of 2:3 as eluant to obtain purified compound II.

5. The preparation method according to claim 1, wherein a preparation method of the compound A comprises the following steps:

step one, providing compound C and D represented by the following formulas,

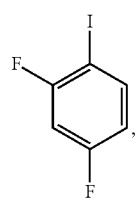

C

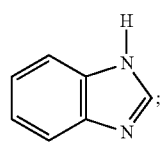

D step two, performing Ullmann coupling reaction between the compound C and the compound D under anaerobic condition in presence of catalyst to obtain compound E, the reaction equation being:

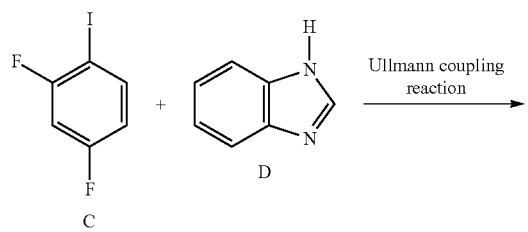

-continued

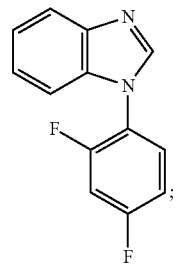

E step three, reacting the compound E with an alkyl iodide in a solvent to obtain the compound A, the reaction equation being:

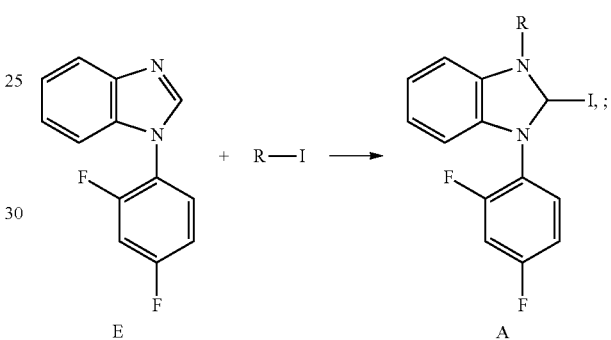

Wherein R—I is alkyl iodide, R is $C_1$-$C_8$ alkyl.

6. The preparation method according to claim 5, wherein in step two the reaction temperature of the Ullmann coupling reaction is from 100° C. to 180° C., the catalyst is a mixed catalyst composed of copper iodide, 1,10-phenanthroline and cesium carbonate, the solvent is N, N-dimethylformamide; the solvent in step three is toluene, the reaction temperature is from 25° C. to 45° C.

7. The preparation method according to claim 5, wherein the step two further comprises steps of separation and purification of compound E: an obtained mixture of the Ullmann coupling reaction is vacuum concentrated; ethyl acetate solution was added to the concentrate to produce a precipitate; the precipitate is separated by filtration and is washed with ethyl acetate, and the filtrate was collected; the filtrate is finally concentrated and is applied to silica gel column chromatography using a mixture solution containing ethyl acetate and n-hexane in a volume ratio of 2:3 as eluant, and the purified compound E is obtained.

8. The preparation method according to claim 5, wherein the step three further comprises steps of separation and purification of compound A: the crude reaction product of step three is filtrated, the filtrated precipitate is washed with toluene and dried to obtain the purified compound A.

* * * * *